United States Patent [19]
Russell et al.

[11] Patent Number: 5,919,638
[45] Date of Patent: Jul. 6, 1999

[54] REAGENTS AND METHODS USEFUL FOR DETECTING PROSTATE TUMORS

[75] Inventors: John C. Russell, Pleasant Prairie, Wis.; Maurice Cohen, Highland Park, Ill.; Paula N. Friedman, Deerfield, Ill.; Michael R. Klass, Libertyville, Ill.; Lisa Roberts-Rapp, Gurnee, Ill.

[73] Assignee: Abbott Laboratories, Abbott Park, Ill.

[21] Appl. No.: 08/727,688

[22] Filed: Oct. 8, 1996

[51] Int. Cl.$^6$ .......................... C12Q 1/68; G01N 33/574; C07M 21/04; C12P 19/34
[52] U.S. Cl. ............................ 435/7.23; 435/6; 435/91.2; 436/504; 536/23.1; 536/23.5
[58] Field of Search ................................... 436/504, 7.23; 435/6, 91.2; 536/23.1, 23.5

[56] References Cited

FOREIGN PATENT DOCUMENTS

| 0655498 | 5/1995 | European Pat. Off. |
| 9520681 | 8/1995 | WIPO |
| 9528498 | 10/1995 | WIPO |
| 9621042 | 7/1996 | WIPO |
| 9623079 | 8/1996 | WIPO |

OTHER PUBLICATIONS

Ac. No. HS835158, Jul. 1995, Hillier, et al., XP002053784.
Ac. No. HS836158, Jul. 1995, Hillier, et al., XP002053785.
Ac. No. HS660266, Jan. 1996, Hillier, et al., XP002053786.
Ac. No. HS363118, May 1995, Waye, et al., XP002053787.
Ac. No. T25991, Oct. 1996, Matsubara, et al., XP002053788.

*Primary Examiner*—Lila Feisee
*Assistant Examiner*—Geetha P. Bansal
*Attorney, Agent, or Firm*—Cheryl L. Becker

[57] ABSTRACT

A set of contiguous and partially overlapping oligonucleotide sequences transcribed from a prostate. Also provided are human disease-specific polypeptides translated from said oligonucleotide sequences and a procedure for producing such polypeptide by recombinant techniques. Antibodies, antagonists and inhibitors of such polypeptide which may be used to prevent the action of such polypeptide and therefore may be used therapeutically to treat prostate diseases, tumors or metastastases are disclosed. Also disclosed is the use of said antibodies, agonists and inhibitors as well as the nucleic acid sequences to screen for, diagnose, prognose, stage and monitor conditions and diseases attributable to prostate tumor, especially prostate cancer. The use of said partial sequence to provide antibodies, agonists and inhibitors as well as partial nucleic acid sequences to screen for, diagnose, stage and monitor diseases and associated with prostate tumor. Illustrative sequences and clone designations for prostate tumors are provided.

10 Claims, 10 Drawing Sheets

```
>g885075
TGCGCNGGAG CCTGAGCGGA GGGTGTGCGC AGCCTCGCCA GCGGGGGCCC CGGGCTGNGC
TGCGCNGGAG CCTGAGCGGA GGGTGTGCGC AGCCTCGCCA GCGGGGGCCC CGGGCTGNGC  (Cons)

>g885075
CATTGCCTCA CTGAGCCAGC GCCTGCCTNC TACCTCGCCG ACAGCTGGAA CCAGTGCGAC
CATTGCCTCA CTGAGCCAGC GCCTGCCTNC TACCTCGCCG ACAGCTGGAA CCAGTGCGAC  (Cons)

>g885075
CTAGTGGCTC TCACCTGCTT CCTCCTGGGC GTGGGCTGCC GGCTGACCCC GGGTTTGTAC
CTAGTGGCTC TCACCTGCTT CCTCCTGGGC GTGGGCTGCC GGCTGACCCC GGGTTTGTAC  (Cons)

>g885075
CACCTGGGCC GCACTGTCCT CTGCATCGAC TTCATGGTTT TCACGGTGCG GCTGCTTCAC
CACCTGGGCC GCACTGTCCT CTGCATCGAC TTCATGGTTT TCACGGTGCG GCTGCTTCAC  (Cons)
```

FIG.1A-1

```
>g885075
ATCTTCACGG TCAACAAACA GCTGGGGCCC AAGATCGTCA TCGTGAGCAA GATGATGAAG
>1512846
              CAAACA GCTGGGGCCC AAGATCGTCA TCGTGAGCAA GATGATGAAG
>1699634
                                 AAGATCGTCA TCGTGAGCAA GATGATGAAG
ATCTTCACGG TCAACAAACA GCTGGGGCCC AAGATCGTCA TCGTGAGCAA GATGATGAAG   (Cons)

>g885075
GACGTGTTCT TCTTCCTCTT CTTCCTCGGC GTGTGGCTGG TAGC:TATGG GTTGGGCCAC
>1512846
GACGTGTTCT TCTTCCTCTT CTTCCTCGGC GTGTGGCTGG TAGCCTATGG CGTGG:CCAC
>1699634
GACGTGTTCT TCTTCCTCTT CTTCCTCGGC GTGTGGCTGG TAGCCTATGG CGTGG:CCAC
GACGTGTTCT TCTTCCTCTT CTTCCTCGGC GTGTGGCTGG TAGCCTATGG CGTGG:CCAC   (Cons)
```

FIG.1A-2

```
>g885075
GGAGGGGT
>1512846
GGAGGGGCTC  CTGAGGCCAC  GGGACAGTGA  CTTCCCAAGT  ATCCTGCGCC  GCGTCTTCTA
>1699634
GGAGGGGCTC  CTGAGGCCAC  GGGACAGTGA  CTTCCCAAGT  ATCCTGCGCC  GCGTCTTCTA
GGAGGGGCTC  CTGAGGCCAC  GGGACAGTGA  CTTCCCAAGT  ATCCTGCGCC  GCGTCTTCTA  (Cons)
```

FIG.1A-3

```
>1512846
CCGTCCCTAC  CTGCAGATCT  TCGGGCAGAT  TCCCCAGGAG  GACATGGAC
>1699634
CCGTCCCTAC  CTGCAGATCT  TCGGGCAGAT  TCCCCAGGAG  GACATGGACG  TGGCCCTCAT
>1444924
                                    CCAGGAG  GACATGGACG  TGGCCCTCAT
CCGTCCCTAC  CTGCAGATCT  TCGGGCAGAT  TCCCCAGGAG  GACATGGACG  TGGCCCTCAT  (Cons)

>1699634
GGAG
>1444924
GGAGCACAGC  AACTGCTCGT  CGGAGCCCGG  CTTCTGGGCA  CACCCTCCTG  GGGCCCAGGC
GGAGCACAGC  AACTGCTCGT  CGGAGCCCGG  CTTCTGGGCA  CACCCTCCTG  GGGCCCAGGC  (Cons)

>1444924
GGGCACCTGC  GTCTCCCAGT  ATGCCAACTG  GCTGGTGGTG  CTGCTCCCTCG  TCATCTTCCT
GGGCACCTGC  GTCTCCCAGT  ATGCCAACTG  GCTGGTGGTG  CTGCTCCCTCG  TCATCTTCCT
```

FIG.1A-4

```
>1444924
GCTCGTGGCC  AACATCCTGC  TGGTCAACTT  GCTCATTGCC  ATGTTCAGTT  ACACATTCGG
GCTCGTGGCC  AACATCCTGC  TGGTCAACTT  GCTCATTGCC  ATGTTCAGTT  ACACATTCGG  (Cons)

>1444924
CAAAGTACAG  GGCAACAGCG  ATCTCTACTG  GAAGGCGCAN  GTTACCGC
>1209763
            GCG  ATCTCTACTG  GAAGGCGCAG  GTTACCGCCT  CATCCGGGAA
CAAAGTACAG  GGCAACAGCG  ATCTCTACTG  GAAGGCGCAG  GTTACCGCCT  CATCCGGGAA  (Cons)

>1209763
TTCCACTCTC  GGCCCGCGCT  GGCCCCGCCC  TTTATCGTCA  TCTCCCACTT  GCGCCTCCTG
TTCCACTCTC  GGCCCGCGCT  GGCCCCGCCC  TTTATCGTCA  TCTCCCACTT  GCGCCTCCTG  (Cons)
```

FIG. 1A-5

```
>1209763
CTCAGGCAAT TGTGCAGGCG ACCCCGGAGC CCCCAGCCGT CCTCCCCGGC CCTCGAGCAT
CTCAGGCAAT TGTGCAGGCG ACCCCGGAGC CCCCAGCCGT CCTCCCCGGC CCTCGAGCAT  (Cons)

>1209763
TTCCGGGTTT ACCTTTCTAA GGAAGCCGAG CGGAAGCTGC TAACGTGGGA ATCGGTGCAT
>612079                                                      GCAT
TTCCGGGTTT ACCTTTCTAA GGAAGCCGAG CGGAAGCTGC TAACGTGGGA ATCGGTGCAT  (Cons)
```

FIG.1A-6

```
>1209763
AAGGAGAACT TTCTGCTGGC ACG
>612079
AAGGAGAACT TTCTGCTGGC ACGCGCTAGG GACAAGCGGG AGAGCGACTC CGAGCGTCTG
>608177
                 GGC ACGCGCTAGG GACAAGCGGG AGAGCGACTC CGAGCGTCTG
AAGGAGAACT TTCTGCTGGC ACGCGCTAGG GACAAGCGGG AGAGCGACTC CGAGCGTCTG  (Cons)

>612079
AAGCGCACGT CCCAGAAGGT GGACTTGGCA CTGAAACAGC TGGGACACAT CCGCGAGTAC
>608177
AAGCGCACGT CCCAGAAGGT GGACTTGGCA CTGAAACAGC TGGGACACAT CCGCGAGTAC
AAGCGCACGT CCCAGAAGGT GGACTTGGCA CTGAAACAGC TGGGACACAT CCGCGAGTAC  (Cons)
```

FIG. 1A-7

```
>612079                                                                                          
         GAACAGCGCC TGAAAGTGCT GGAGCGGGAG GTCCAGCAGT GTAGCCGCGT CCTGGGGTGG
>608177                                                                                          
         GAACAGCGCC TGAAAGTGCT GGAGCGGGAG GTCCAGCAGT GTAGCCGCGT CCTGGGGTGG
>842007                                                                                          
                               GCGGGAG GTCCAGCAGT GTAGCCGCGT CCTGGGGTGG
         GAACAGCGCC TGAAAGTGCT GGAGCGGGAG GTCCAGCAGT GTAGCCGCGT CCTGGGGTGG  (Cons)

>612079                                                                                          
         GTGGCCGAGG CCCTGAGCCG NTCTGCCTTG CTGCCCCCAG GTGGGCCGNC ANCCNNTGAC
>608177                                                                                          
         GTGGCCGAGG CCCTGAGCCG CTCTGCCTTG CTGCCCCCAG GTGGGCCGCC ACCCCCTGAC
>842007                                                                                          
         GTGGCCGAGG CCCTGAGCCG CTCTGCCTTG CTGCCCCCAG GTGGGCCGNC ACCCNCTGAC
         GTGGCCGAGG CCCTGAGCCG CTCTGCCTTG CTGCCCCCAG GTGGGCCGCC ACCCCCTGAC  (Cons)
```

FIG.1A-8

```
>612079
CTGCCTGGGT CCA

>608177
CTGCCTGGGT CCAAAGA

>842007
CTGCCTGGGT CCAAAGACTG AGCCCTGCTG GCGGACTTCA AGGAGAAGCC CCCACAGGGG
CTGCCTGGGT CCAAAGACTG AGCCCTGCTG GCGGACTTCA AGGAGAAGCC CCCACAGGGG  (Cons)

>842007
ATTTGCTCC TAGAGTAAGG CTCATCTGGG CCTNGGCCCC NGCACCTGGT GGCCTTGTCC
ATTTGCTCC TAGAGTAAGG CTCATCTGGG CCTNGGCCCC NGCACCTGGT GGCCTTGTCC  (Cons)

>842007
TTGAGGTGAG CCCCATGTNC ATCTGGGNCA NTGTCAGG
TTGAGGTGAG CCCCATGTNC ATCTGGGNCA NTGTCAGG  (Cons)
```

FIG.1A-9

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 367 base pairs
      (B) TYPE: nucleic acid
      (C) STRANDEDNESS: single
      (D) TOPOLOGY: linear (xi) SEQUENCE DESCRIPTION: SEQ ID NO:1:

```
TGCGCNGGAG CCTGAGCGGA GGGTGTGCGC AGCCTCGCCA GCGGGGCCC  CGGGCTGNGC    60

CATTGCCTCA CTGAGCCAGC GCCTGCCTNC TACCTCGCCG ACAGCTGGAA CCAGTGCGAC   120

CTAGTGGCTC TCACCTGCTT CCTCCTGGGC GTGGGCTGCC GGCTGACCCC GGGTTTGTAC   180

CACCTGGGCC GCACTGTCCT CTGCATCGAC TTCATGGTTT TCACGGTGCG GCTGCTTCAC   240

ATCTTCACGG TCAACAAACA GCTGGGGCCC AAGATCGTCA TCGTGAGCAA GATGATGAAG   300

GACGTGTTCT TCTTCCTCTT CTTCCTCGGC GTGTGGCTGG TAGCTATGGG TTGGGCCACG   360

GAGGGGT                                                             367
```

(2) INFORMATION FOR SEQ ID NO:2:

(i) SEQUENCE CHARACTERISTICS:
      (A) LENGTH: 214 base pairs
      (B) TYPE: nucleic acid
      (C) STRANDEDNESS: single
      (D) TOPOLOGY: linear (xi) SEQUENCE DESCRIPTION: SEQ ID NO:2:

```
CAAACAGCTG GGGCCCAAGA TCGTCATCGT GAGCAAGATG ATGAAGGACG TGTTCTTCTT    60

CCTCTTCTTC CTCGGCGTGT GGCTGGTAGC CTATGGCGTG GCCACGGAGG GGCTCCTGAG   120

GCCACGGGAC AGTGACTTCC CAAGTATCCT GCGCCGCGTC TTCTACCGTC CCTACCTGCA   180

GATCTTCGGG CAGATTCCCC AGGAGGACAT GGAC                               214
```

(2) INFORMATION FOR SEQ ID NO:3:

(i) SEQUENCE CHARACTERISTICS:
      (A) LENGTH: 213 base pairs
      (B) TYPE: nucleic acid
      (C) STRANDEDNESS: single
      (D) TOPOLOGY: linear (xi) SEQUENCE DESCRIPTION: SEQ ID NO:3:

```
AAGATCGTCA TCGTGAGCAA GATGATGAAG GACGTGTTCT TCTTCCTCTT CTTCCTCGGC    60

GTGTGGCTGG TAGCCTATGG CGTGGCCACG GAGGGGCTCC TGAGGCCACG GGACAGTGAC   120

TTCCCAAGTA TCCTGCGCCG CGTCTTCTAC CGTCCCTACC TGCAGATCTT CGGGCAGATT   180

CCCCAGGAGG ACATGGACGT GGCCCTCATG GAG                                213
```

(2) INFORMATION FOR SEQ ID NO:4:

(i) SEQUENCE CHARACTERISTICS:
      (A) LENGTH: 255 base pairs
      (B) TYPE: nucleic acid
      (C) STRANDEDNESS: single
      (D) TOPOLOGY: linear (xi) SEQUENCE DESCRIPTION: SEQ ID NO:4:

```
CCAGGAGGAC ATGGACGTGG CCCTCATGGA GCACAGCAAC TGCTCGTCGG AGCCCGGCTT    60

CTGGGCACAC CCTCCTGGGG CCCAGGCGGG CACCTGCGTC TCCCAGTATG CCAACTGGCT   120

GGTGGTGCTG CTCCTCGTCA TCTTCCTGCT CGTGGCCAAC ATCCTGCTGG TCAACTTGCT   180

CATTGCCATG TTCAGTTACA CATTCGGCAA AGTACAGGGC AACAGCGATC TCTACTGGAA   240

GGCGCANGTT ACCGC                                                    255
```

(2) INFORMATION FOR SEQ ID NO:5:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (xi) SEQUENCE DESCRIPTION: SEQ ID NO:5:

```
GCGATCTCTA CTGGAAGGCG CAGGTTACCG CCTCATCCGG GAATTCCACT CTCGGCCCGC    60

GCTGGCCCCG CCCTTTATCG TCATCTCCCA CTTGCGCCTC CTGCTCAGGC AATTGTGCAG   120

GCGACCCCGG AGCCCCCAGC CGTCCTCCCC GGCCCTCGAG CATTTCCGGG TTTACCTTTC   180

TAAGGAAGCC GAGCGGAAGC TGCTAACGTG GGAATCGGTG CATAAGGAGA ACTTTCTGCT   240

GGCACG                                                              246
```

(2) INFORMATION FOR SEQ ID NO:6:

(i) SEQUENCE CHARACTERISTICS:
        (A) LENGTH: 257 base pairs
        (B) TYPE: nucleic acid
        (C) STRANDEDNESS: single
        (D) TOPOLOGY: linear (xi) SEQUENCE DESCRIPTION: SEQ ID NO:6:

```
GCATAAGGAG AACTTTCTGC TGGCACGCGC TAGGGACAAG CGGGAGAGCG ACTCCGAGCG    60

TCTGAAGCGC ACGTCCCAGA AGGTGGACTT GGCACTGAAA CAGCTGGGAC ACATCCGCGA   120

GTACGAACAG CGCCTGAAAG TGCTGGAGCG GGAGGTCCAG CAGTGTAGCC GCGTCCTGGG   180

GTGGGTGGCC GAGGCCCTGA GCCGNTCTGC CTTGCTGCCC CCAGGTGGGC CGNCANCCNN   240

TGACCTGCCT GGGTCCA                                                  257
```

(2) INFORMATION FOR SEQ ID NO:7:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (xi) SEQUENCE DESCRIPTION: SEQ ID NO:7:

```
GGCACGCGCT AGGGACAAGC GGGAGAGCGA CTCCGAGCGT CTGAAGCGCA CGTCCCAGAA    60

GGTGGACTTG GCACTGAAAC AGCTGGGACA CATCCGCGAG TACGAACAGC GCCTGAAAGT   120

GCTGGAGCGG GAGGTCCAGC AGTGTAGCCG CGTCCTGGGG TGGGTGGCCG AGGCCCTGAG   180

CCGCTCTGCC TTGCTGCCCC CAGGTGGGCC GCCACCCCCT GACCTGCCTG GGTCCAAAGA   240
```

(2) INFORMATION FOR SEQ ID NO:8:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (xi) SEQUENCE DESCRIPTION: SEQ ID NO:8:

```
GCGGGAGGTC CAGCAGTGTA GCCGCGTCCT GGGGTGGGTG GCCGAGGCCC TGAGCCGCTC      60

TGCCTTGCTG CCCCCAGGTG GGCCGNCACC CNCTGACCTG CCTGGGTCCA AAGACTGAGC     120

CCTGCTGGCG GACTTCAAGG AGAAGCCCCC ACAGGGGATT TTGCTCCTAG AGTAAGGCTC     180

ATCTGGGCCT NGGCCCCNGC ACCTGGTGGC CTTGTCCTTG AGGTGAGCCC CATGTNCATC     240

TGGGNCANTG TCAGG                                                     255
```

(2) INFORMATION FOR SEQ ID NO:9:

(i) SEQUENCE CHARACTERISTICS:
        (A) LENGTH: 1297 base pairs
        (B) TYPE: nucleic acid
        (C) STRANDEDNESS: single
        (D) TOPOLOGY: linear (xi) SEQUENCE DESCRIPTION: SEQ ID NO:9:

```
TGCGCNGGAG CCTGAGCGGA GGGTGTGCGC AGCCTCGCCA GCGGGGGCCC CGGGCTGNGC      60

CATTGCCTCA CTGAGCCAGC GCCTGCCTNC TACCTCGCCG ACAGCTGGAA CCAGTGCGAC     120

CTAGTGGCTC TCACCTGCTT CCTCCTGGGC GTGGGCTGCC GGCTGACCCC GGGTTTGTAC     180

CACCTGGGCC GCACTGTCCT CTGCATCGAC TTCATGGTTT TCACGGTGCG GCTGCTTCAC     240

ATCTTCACGG TCAACAAACA GCTGGGCCC AAGATCGTCA TCGTGAGCAA GATGATGAAG      300

GACGTGTTCT TCTTCCTCTT CTTCCTCGGC GTGTGGCTGG TAGCCTATGG CGTGGCCACG     360

GAGGGGCTCC TGAGGCCACG GGACAGTGAC TTCCCAAGTA TCCTGCGCCG CGTCTTCTAC     420

CGTCCCTACC TGCAGATCTT CGGGCAGATT CCCCAGGAGG ACATGGACGT GGCCCTCATG     480

GAGCACAGCA ACTGCTCGTC GGAGCCCGGC TTCTGGGCAC ACCCTCCTGG GGCCCAGGCG     540

GGCACCTGCG TCTCCCAGTA TGCCAACTGG CTGGTGGTGC TGCTCCTCGT CATCTTCCTG     600

CTCGTGGCCA ACATCCTGCT GGTCAACTTG CTCATTGCCA TGTTCAGTTA CACATTCGGC     660

AAAGTACAGG GCAACAGCGA TCTCTACTGG AAGGCGCAGG TTACCGCCTC ATCCGGGAAT     720

TCCACTCTCG GCCCGCGCTG GCCCCGCCCT TTATCGTCAT CTCCCACTTG CGCCTCCTGC     780

TCAGGCAATT GTGCAGGCGA CCCCGGAGCC CCCAGCCGTC CTCCCCGGCC CTCGAGCATT     840

TCCGGGTTTA CCTTTCTAAG GAAGCCGAGC GGAAGCTGCT AACGTGGGAA TCGGTGCATA     900

AGGAGAACTT TCTGCTGGCA CGCGCTAGGG ACAAGCGGGA GAGCGACTCC GAGCGTCTGA     960

AGCGCACGTC CCAGAAGGTG GACTTGGCAC TGAAACAGCT GGGACACATC CGCGAGTACG    1020

AACAGCGCCT GAAAGTGCTG GAGCGGGAGG TCCAGCAGTG TAGCCGCGTC CTGGGGTGGG    1080

TGGCCGAGGC CCTGAGCCGC TCTGCCTTGC TGCCCCCAGG TGGGCCGCCA CCCCCTGACC    1140

TGCCTGGGTC CAAAGACTGA GCCCTGCTGG CGGACTTCAA GGAGAAGCCC CACAGGGGA     1200

TTTTGCTCCT AGAGTAAGGC TCATCTGGGC CTNGGCCCCN GCACCTGGTG GCCTTGTCCT    1260

TGAGGTGAGC CCCATGTNCA TCTGGGNCAN TGTCAGG                            1297
```

(2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:10:

Cys Ala Gly Ala
 1

(2) INFORMATION FOR SEQ ID NO:11:

(i) SEQUENCE CHARACTERISTICS:
        (A) LENGTH: 300 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:11:

```
Ala Glu Gly Val Arg Ser Leu Ala Ser Gly Gly Pro Gly Leu Xaa His
 1               5                  10                  15

Cys Leu Thr Glu Pro Ala Pro Ala Xaa Tyr Leu Ala Asp Ser Trp Asn
             20                  25                  30

Gln Cys Asp Leu Val Ala Leu Thr Cys Phe Leu Leu Gly Val Gly Cys
         35                  40                  45

Arg Leu Thr Pro Gly Leu Tyr His Leu Gly Arg Thr Val Leu Cys Ile
     50                  55                  60

Asp Phe Met Glu Thr Val Phe Thr Val Arg Leu Leu His Ile Phe Thr
 65                  70                  75                  80

Val Asn Lys Gln Leu Gly Pro Lys Ile Val Ile Val Ser Lys Met Glu
                 85                  90                  95

Thr Met Glu Thr Lys Asp Val Phe Phe Phe Leu Phe Phe Leu Gly Val
             100                 105                 110

Trp Leu Val Ala Tyr Gly Val Ala Thr Glu Gly Leu Leu Arg Pro Arg
         115                 120                 125

Asp Ser Asp Phe Pro Ser Ile Leu Arg Arg Val Phe Tyr Arg Pro Tyr
     130                 135                 140

Leu Gln Ile Phe Gly Gln Ile Pro Gln Glu Asp Met Glu Thr Asp Val
145                 150                 155                 160

Ala Leu Met Glu Thr Glu His Ser Asn Cys Ser Ser Glu Pro Gly Phe
                 165                 170                 175

Trp Ala His Pro Pro Gly Ala Gln Ala Gly Thr Cys Val Ser Gln Tyr
             180                 185                 190

Ala Asn Trp Leu Val Val Leu Leu Val Ile Phe Leu Leu Val Ala
         195                 200                 205

Asn Ile Leu Leu Val Asn Leu Leu Ile Ala Met Glu Thr Phe Ser Tyr
     210                 215                 220

Thr Phe Gly Lys Val Gln Gly Asn Ser Asp Leu Tyr Trp Lys Ala Gln
225                 230                 235                 240

Val Thr Ala Ser Ser Gly Asn Ser Thr Leu Gly Pro Arg Trp Pro Arg
                 245                 250                 255

Pro Leu Ser Ser Ser Pro Thr Cys Ala Ser Cys Ser Gly Asn Cys Ala
             260                 265                 270

Gly Asp Pro Gly Ala Pro Ser Arg Pro Pro Arg Pro Ser Ser Ile Ser
         275                 280                 285

Gly Phe Thr Phe Leu Arg Lys Pro Ser Gly Ser Cys
     290                 295                 300
```

(2) INFORMATION FOR SEQ ID NO:12:

(i) SEQUENCE CHARACTERISTICS:
        (A) LENGTH: 25 amino acids
        (B) TYPE: amino acid 5,919,638

57

58

-continued

```
            (C) STRANDEDNESS: single
            (D) TOPOLOGY: linear (ii) MOLECULE TYPE: None (xi) SEQUENCE DESCRIPTION: SEQ ID NO:12:

Arg Gly Asn Arg Cys Ile Arg Arg Thr Phe Cys Trp His Ala Leu Gly
1               5                   10                  15

Thr Ser Gly Arg Ala Thr Pro Ser Val
            20                  25

(2) INFORMATION FOR SEQ ID NO:13:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:13:

Ser Ala Arg Pro Arg Arg Trp Thr Trp His
1               5                   10

(2) INFORMATION FOR SEQ ID NO:14:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:14:

Asn Ser Trp Asp Thr Ser Ala Ser Thr Asn Ser Ala
1               5                   10

(2) INFORMATION FOR SEQ ID NO:15:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:15:

Lys Cys Trp Ser Gly Arg Ser Ser Val Ala Ala Ser Trp Gly Gly
1               5                   10                  15

Trp Pro Arg Pro
            20

(2) INFORMATION FOR SEQ ID NO:16:

(i) SEQUENCE CHARACTERISTICS:
            (A) LENGTH: 38 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:16:

Ala Ala Leu Pro Cys Cys Pro Gln Val Gly Arg His Pro Leu Thr Cys
1               5                   10                  15
```

```
Leu Gly Pro Lys Thr Glu Pro Cys Trp Arg Thr Ser Arg Arg Ser Pro
            20                  25                  30

His Arg Gly Phe Cys Ser
        35
```

(2) INFORMATION FOR SEQ ID NO:17:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:17:

```
Ser Lys Ala His Leu Gly Leu Gly Pro Xaa Thr Trp Trp Pro Cys Pro
1               5                   10                  15
```

(2) INFORMATION FOR SEQ ID NO:18:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:18:

```
Gly Glu Pro His Val His Leu Gly Xaa Cys Gln
1               5                   10
```

(2) INFORMATION FOR SEQ ID NO:19:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:19:

```
Ala Xaa Glu Pro Glu Arg Arg Val Cys Ala Ala Ser Pro Ala Gly Ala
1               5                   10                  15

Pro Gly Xaa Ala Ile Ala Ser Leu Ser Gln Arg Leu Pro Xaa Thr Ser
            20                  25                  30

Pro Thr Ala Gly Thr Ser Ala Thr
        35                  40
```

(2) INFORMATION FOR SEQ ID NO:20:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:20:

```
Trp Leu Ser Pro Ala Ser Ser Trp Ala Ala Gly
1               5                   10
```

(2) INFORMATION FOR SEQ ID NO:21:

(i) SEQUENCE CHARACTERISTICS:

(A) LENGTH: 39 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:21:

Pro Arg Val Cys Thr Thr Trp Ala Ala Leu Ser Ser Ala Ser Thr Ser
1               5                  10                  15

Trp Phe Ser Arg Cys Gly Cys Phe Thr Ser Ser Arg Ser Thr Asn Ser
            20                  25                  30

Trp Gly Pro Arg Ser Ser Ser
            35

(2) INFORMATION FOR SEQ ID NO:22:

(i) SEQUENCE CHARACTERISTICS:
            (A) LENGTH: 2 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:22:

Ala Arg
1

(2) INFORMATION FOR SEQ ID NO:23:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:23:

Arg Thr Cys Ser Ser Ser Ser Ser Ser Ser Ala Cys Gly Trp
1               5                  10

(2) INFORMATION FOR SEQ ID NO:24:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:24:

Pro Met Glu Thr Ala Trp Pro Arg Arg Gly Ser
1               5                  10

(2) INFORMATION FOR SEQ ID NO:25:

(i) SEQUENCE CHARACTERISTICS:
            (A) LENGTH: 163 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:25:

```
Gly His Gly Thr Val Thr Ser Gln Val Ser Cys Ala Ala Ser Ser Thr
  1               5                  10                 15

Val Pro Thr Cys Arg Ser Ser Gly Arg Phe Pro Arg Arg Thr Trp Thr
             20              25              30

Trp Pro Ser Trp Ser Thr Ala Thr Ala Arg Arg Ser Pro Ala Ser Gly
         35              40              45

His Thr Leu Leu Gly Pro Arg Arg Ala Pro Ala Ser Pro Ser Met Glu
 50                  55              60

Thr Pro Thr Gly Trp Trp Cys Cys Ser Ser Ser Ser Cys Ser Trp
 65              70              75              80

Pro Thr Ser Cys Trp Ser Thr Cys Ser Leu Pro Cys Ser Val Thr His
             85              90              95

Ser Ala Lys Tyr Arg Ala Thr Ala Ile Ser Thr Gly Arg Arg Arg Leu
            100             105             110

Pro Pro His Pro Gly Ile Pro Leu Ser Ala Arg Ala Gly Pro Ala Leu
            115             120             125

Tyr Arg His Leu Pro Leu Ala Pro Pro Ala Gln Ala Ile Val Gln Ala
            130             135             140

Thr Pro Glu Pro Pro Ala Val Leu Pro Gly Pro Arg Ala Phe Pro Gly
145             150             155             160

Leu Pro Phe (2) INFORMATION FOR SEQ ID NO:26:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:26:

Gly Ser Arg Ala Glu Ala Ala Asn Val Gly Ile Gly Ala
 1               5                  10

(2) INFORMATION FOR SEQ ID NO:27:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:27:

Gly Glu Leu Ser Ala Gly Thr Arg
 1               5

(2) INFORMATION FOR SEQ ID NO:28:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:28:

Gly Gln Ala Gly Glu Arg Leu Arg Ala Ser Glu Ala His Val Pro Glu
 1               5                  10                 15
```

```
Gly Gly Leu Gly Thr Glu Thr Ala Gly Thr His Pro Arg Val Arg Thr
        20                  25                  30

Ala Pro Glu Ser Ala Gly Ala Gly Gly Pro Ala Val
        35                  40
```

(2) INFORMATION FOR SEQ ID NO:29:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:29:

```
Pro Arg Pro Gly Val Gly Gly Arg Gly Pro Glu Pro Leu Cys Leu Ala
  1               5                  10                  15

Ala Pro Arg Trp Ala Ala Thr Pro
        20
```

(2) INFORMATION FOR SEQ ID NO:30:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:30:

```
Pro Ala Trp Val Gln Arg Leu Ser Pro Ala Gly Gly Leu Gln Gly Glu
  1               5                  10                  15

Ala Pro Thr Gly Asp Phe Ala Pro Arg Val Arg Leu Ile Trp Ala Xaa
        20                  25                  30

Ala Pro Ala Pro Gly Gly Leu Val Leu Glu Val Ser Pro Met Glu Thr
        35                  40                  45

Xaa Ile Trp Xaa Xaa Val Arg
        50                  55
```

(2) INFORMATION FOR SEQ ID NO:31:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:31:

```
Arg Xaa Ser Leu Ser Gly Gly Cys Ala Gln Pro Arg Gln Arg Gly Pro
  1               5                  10                  15

Arg Ala Xaa Pro Leu Pro His
        20
```

(2) INFORMATION FOR SEQ ID NO:32:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:32:

| | | | | | | | | | | | | | | |
|---|---|---|---|---|---|---|---|---|---|---|---|---|---|---|
|Ala|Ser|Ala|Cys|Leu|Leu|Pro|Arg|Arg|Gln|Leu|Glu|Pro|Val|Arg|Pro|
|1| | | |5| | | | |10| | | | |15| |

| | | | | | | | | | | | | | | |
|---|---|---|---|---|---|---|---|---|---|---|---|---|---|---|
|Ser|Gly|Ser|His|Leu|Leu|Pro|Pro|Gly|Arg|Gly|Leu|Pro|Ala|Asp|Pro|
| | | |20| | | | |25| | | | |30| | |

| | | | | | | | | | | | | | | |
|---|---|---|---|---|---|---|---|---|---|---|---|---|---|---|
|Gly|Phe|Val|Pro|Pro|Gly|Pro|His|Cys|Pro|Leu|His|Arg|Leu|His|Gly|
| | |35| | | | |40| | | | |45| | | |

| | | | | | | | | | | | | | | |
|---|---|---|---|---|---|---|---|---|---|---|---|---|---|---|
|Phe|His|Gly|Ala|Ala|Ala|Ser|His|Leu|His|Gly|Gln|Gln|Thr|Ala|Gly|
| |50| | | | |55| | | | |60| | | | |

Ala Gln Asp Arg His Arg Glu Gln Asp Asp Glu Gly Arg Val Leu Leu
65                  70                  75                  80

Pro Leu Leu Pro Arg Arg Val Ala Gly Ser Leu Trp Arg Gly His Gly
                85                  90                  95

Gly Ala Pro Glu Ala Thr Gly Gln
            100

(2) INFORMATION FOR SEQ ID NO:33:

(i) SEQUENCE CHARACTERISTICS:
        (A) LENGTH: 256 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:33:

Leu Pro Lys Tyr Pro Ala Pro Arg Leu Leu Pro Ser Leu Pro Ala Asp
1               5                   10                  15

Leu Arg Ala Asp Ser Pro Gly Gly His Gly Arg Gly Pro His Gly Ala
                20                  25                  30

Gln Gln Leu Leu Val Gly Ala Arg Leu Leu Gly Thr Pro Ser Trp Gly
            35                  40                  45

Pro Gly Gly His Leu Arg Leu Pro Val Cys Gln Leu Ala Gly Gly Ala
        50                  55                  60

Ala Pro Arg His Leu Pro Ala Arg Gly Gln His Pro Ala Gly Gln Leu
65                  70                  75                  80

Ala His Cys His Val Gln Leu His Ile Arg Gln Ser Thr Gly Gln Gln
                85                  90                  95

Arg Ser Leu Leu Glu Gly Ala Gly Tyr Arg Leu Ile Arg Glu Phe His
            100                 105                 110

Ser Arg Pro Ala Leu Ala Pro Pro Phe Ile Val Ile Ser His Leu Arg
        115                 120                 125

Leu Leu Leu Arg Gln Leu Cys Arg Arg Pro Arg Ser Pro Gln Pro Ser
130                 135                 140

Ser Pro Ala Leu Glu His Phe Arg Val Tyr Leu Ser Lys Glu Ala Glu
145                 150                 155                 160

Arg Lys Leu Leu Thr Trp Glu Ser Val His Lys Glu Asn Phe Leu Leu
                165                 170                 175

Ala Arg Ala Arg Asp Lys Arg Glu Ser Asp Ser Glu Arg Leu Lys Arg
            180                 185                 190

Thr Ser Gln Lys Val Asp Leu Ala Leu Lys Gln Leu Gly His Ile Arg
        195                 200                 205

Glu Tyr Glu Gln Arg Leu Lys Val Leu Glu Arg Glu Val Gln Gln Cys
    210                 215                 220

Ser Arg Val Leu Gly Trp Val Ala Glu Ala Leu Ser Arg Ser Ala Leu
225                 230                 235                 240

```
Leu Pro Pro Gly Gly Pro Pro Pro Asp Leu Pro Gly Ser Lys Asp
                245                 250                 255
```

(2) INFORMATION FOR SEQ ID NO:34:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:34:

```
Ala Leu Leu Ala Asp Phe Lys Glu Lys Pro Pro Gln Gly Ile Leu Leu
  1               5                  10                  15

Leu Glu
```

(2) INFORMATION FOR SEQ ID NO:35:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:35:

```
Gly Ser Ser Gly Pro Xaa Pro Xaa His Leu Val Ala Leu Ser Leu Arg
  1               5                  10                  15
```

(2) INFORMATION FOR SEQ ID NO:36:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:36:

```
Ala Pro Cys Xaa Ser Gly Xaa Xaa Ser
  1               5
```

REAGENTS AND METHODS USEFUL FOR DETECTING PROSTATE TUMORS

BACKGROUND OF THE INVENTION

The invention relates generally to detecting prostate tumors, and more particularly, relates to reagents such as polynucleotide sequences and the polypeptide sequences encoded therein, as well as methods which utilize these sequences, which are useful for the detection, diagnosis, staging, monitoring, prognosis, prevention or treatment of diseases such as prostate cancer.

Diseases such as cancer traditionally have been diagnosed by visualization of cells in tissue sections under a microscope by highly trained personnel. Interpretation of tissue sections is subjective and diagnosis can be very difficult with the small samples typically obtained for diagnosis. Usually, it is not desirable or possible to obtain a large sample from the patient. Frequently a reliable diagnosis cannot be given; it may be that there is no positive evidence of a carcinoma, but also, no certainty that the patient is actually free from carcinoma. In some cases, additional invasive investigation then is required to establish a diagnosis.

Judgment of prognosis also often relies upon the appearance of cells when viewed under a microscope. Generally, the more abnormal-looking the cellular organization in a primary tumor, the more likely the tumor will later metastasize. The correlation, however, is by no means absolute.

Certain blood tests are available to assist the physician in diagnosis of various types of cancer. For example, Prostate Specific Antigen ("PSA") is a marker which, if present in the circulatory system in elevated levels, indicates the likelihood of prostate disease, either cancer or benign prostatic hyperplasia (BPH). Assays which test for this marker currently are available. Although we discuss PSA, other such markers are available and include but are not limited to carcinoembryonic antigen (CEA) which is a marker for adenocarcinoma and human chorionic gonadotropin (hCG) which is a marker that is useful in the diagnosis of testicular and trophoblastic tumors. Although all of these markers are helpful in diagnosing a certain type of carcinoma, elevated levels are only indicative of and not diagnostic for a certain type of cancer. Also, the effect of treatment on disease is difficult to monitor at times since the circulating levels of the markers may not reflect the actual state of disease in the patient.

It would be advantageous to provide specific methods and reagents for the diagnosis, staging, prognosis, monitoring, prevention or treatment of diseases and conditions associated with prostate tumors such as cancer or to indicate possible predisposition to these conditions. Such methods would include assaying a test sample for products of the gene. Such methods would comprise making cDNA from mRNA in the test sample, amplifying (when necessary) portions of the cDNA corresponding to the gene or a fragment thereof, and detecting the cDNA product as an indication of the presence of the cancer; or detecting translation products of the mRNAs comprising gene sequences as an indication of the presence of the disease. These reagents include polynucleotide(s), or fragment(s) thereof which may be used in diagnostic methods such as reverse transcriptase-polymerase chain reaction (RT-PCR), PCR, or hybridization assays of biopsied tissue; or proteins which are the translation products of such mRNAs; or antibodies directed against these proteins. Such assays would include methods for assaying a sample for product(s) of the gene and detecting the product(s) as an indication of prostate tumor, especially prostate cancer. Drug treatment or gene therapy for conditions or diseases associated with these detected diseases and conditions then can be based on these identified gene sequences or their expressed proteins, and efficacy of any particular therapy can be monitored using the diagnostic methods disclosed herein.

SUMMARY OF THE INVENTION

The present invention provides a method of detecting target polynucleotides of prostate tumor in a test sample which comprises contacting a target polynucleotide specific for prostate tumor with at least one prostate tumor specific polynucleotide or complement thereof provided herein and detecting the presence of the target in the test sample. The polynucleotide is selected from the group consisting of SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8 and SEQUENCE ID NO 9, and fragments thereof. Also, the target prostate tumor nucleotide may be attached to a solid phase prior to a performing step (a).

The present invention also provides a method for amplifying 5' end cDNA of a prostate tumor gene in a test sample, which comprises performing reverse transcription with random primers, amplifying the cDNA obtained by using other oligonucleotide primer(s) of prostate tumor as sense and antisense primer(s) in a first-stage PCR to obtain amplified cDNA and detecting the presence of the prostate tumor amplicon in the test sample. Amplification can be performed by the polymerase chain reaction. Also, the test sample can be attached to a solid phase prior to performing the method. Further, the detection step can comprise utilizing a detectable label capable of generating a measurable signal. The detectable label can be attached to a solid phase.

The present invention further provides a method of detecting prostate tumor in a test sample suspected of containing target prostate tumor, which comprises contacting said test sample with at least one polynucleotide as a sense primer and with at least one polynucleotide as an anti-sense primer and amplifying same to obtain a first stage reaction product; contacting said first stage reaction product with at least one of said polynucleotides of the contacting step and a second polynucleotide, with the proviso that the second oligonucleotide is located 3' to the first oligonucleotide utilized and is of opposite sense to said first oligonucleotide and detecting said prostate tumor target as an indication of the presence of prostate tumor. The amplification may be performed by the polymerase chain reaction. The test sample can be attached to a solid phase prior to performing the method. The detection step also comprises utilizing a detectable label capable of generating a measurable signal, and the detectable label can be attached to a solid phase. Test kits useful for detecting prostate tumor target in a test sample further are provided which comprise a container containing at least one polynucleotide selected from the group consisting of SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8 and SEQUENCE ID NO 9, and fragments and complements thereof. These test kits further comprising containers containing tools useful for collecting test samples such as blood, urine, saliva, and stool. Such tools include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. They may also be treated with or contain preservatives, stabilizers or antimicrobial agents to help maintain the integrity of the specimens.

The present invention provides a purified polynucleotide or fragment thereof derived from a prostate tumor gene capable of selectively hybridizing to the genome of prostate tumor or the complement thereof. The polynucleotide is selected from the group consisting of SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8 and SEQUENCE ID NO 9, and fragments and complements thereof. Further, the polynucleotide can be produced by recombinant techniques. This recombinant comprises a sequence that encodes at least one epitope of prostate tumor and is contained within a recombinant vector. The recombinant polynucleotide further comprises a host cell transformed with said vector.

The present invention further provides a recombinant expression system comprising an open reading frame of DNA or RNA derived from prostate tumor gene wherein said open reading frame comprises a sequence of prostate tumor genome or cDNA and wherein said open reading frame is operably linked to a control sequence compatible with a desired host. This expression system further comprises a cell transformed with said recombinant expression system. Further, the expression system comprises a polypeptide of at least about eight amino acids in length produced by said cell.

The present invention also provides a polypeptide derived from prostate tumor gene comprising an amino acid sequence or fragment thereof. The polypeptide can be produced by recombinant technology, provided in purified form, or produced by synthetic techniques. Also, an antibody directed against at least one epitope of a prostate tumor gene is provided. The antibody can be a polyclonal or monoclonal antibody. Assay kits for determining the presence of prostate tumor antigen or antibody in a test sample comprise a container containing a polypeptide derived from at least one prostate tumor gene are included. The polypeptide of the assay kit comprises an amino acid sequence having at least 35% identity to an amino acid sequence selected from the group consisting of SEQUENCE ID NO 10, SEQUENCE ID NO 11, SEQUENCE ID NO 12, SEQUENCE ID NO 13, SEQUENCE ID NO 14, SEQUENCE ID NO 15, SEQUENCE ID NO 16, SEQUENCE ID NO 17, SEQUENCE ID NO 18, SEQUENCE ID NO 19, SEQUENCE ID NO 20, SEQUENCE ID NO 21, SEQUENCE ID NO 22, SEQUENCE ID NO 23, SEQUENCE ID NO 24, SEQUENCE ID NO 25, SEQUENCE ID NO 26, SEQUENCE ID NO 27, SEQUENCE ID NO 28, SEQUENCE ID NO 29, SEQUENCE ID NO 30, SEQUENCE ID NO 31, SEQUENCE ID NO 32, SEQUENCE ID NO 33, SEQUENCE ID NO 34, SEQUENCE ID NO 35 and SEQUENCE ID NO 36, or fragments thereof. These test kits further comprising containers containing tools useful for collecting test samples such as blood, urine, saliva, and stool. Such tools include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. They may also be treated with or contain preservatives, stabilizers or antimicrobial agents to help maintain the integrity of the specimens. Also, the polypeptide can be attached to a solid phase.

Another assay kit for determining the presence of prostate tumor antigen or antibody in a test sample comprises a container containing an antibody which specifically binds to a prostate tumor antigen, wherein the antigen comprises a prostate tumor epitope encoded by a sequence having at least about 60% sequence similarity to a sequence of prostate tumor gene provided herein. Further, the antigen is selected from the group consisting of SEQUENCE ID NO 10, SEQUENCE ID NO 11, SEQUENCE ID NO 12, SEQUENCE ID NO 13, SEQUENCE ID NO 14, SEQUENCE ID NO 15, SEQUENCE ID NO 16, SEQUENCE ID NO 17, SEQUENCE ID NO 18, SEQUENCE ID NO 19, SEQUENCE ID NO 20, SEQUENCE ID NO 21, SEQUENCE ID NO 22, SEQUENCE ID NO 23, SEQUENCE ID NO 24, SEQUENCE ID NO 25, SEQUENCE ID NO 26, SEQUENCE ID NO 27, SEQUENCE ID NO 28, SEQUENCE ID NO 29, SEQUENCE ID NO 30, SEQUENCE ID NO 31, SEQUENCE ID NO 32, SEQUENCE ID NO 33, SEQUENCE ID NO 34, SEQUENCE ID NO 35 and SEQUENCE ID NO 36, or fragments thereof. These test kits further comprising containers containing tools useful for collecting test samples such as blood, urine, saliva, and stool. Such tools include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. They may also be treated with or contain preservatives, stabilizers or antimicrobial agents to help maintain the integrity of the specimens. The antibody can be attached to a solid phase.

A method for producing a polypeptide which contains at least one prostate tumor epitope is provided, which comprises incubating host cells transformed with an expression vector comprising a sequence encoding a polypeptide characterized by a positive stranded genome wherein said genome comprises an open reading frame (ORF) encoding a polypeptide wherein said polypeptide comprises an amino acid sequence having at least 35% identity to an amino acid sequence of prostate tumor provided herein.

A method for detecting prostate tumor antigen in a test sample suspected of containing prostate tumor also is provided, which comprises contacting the test sample with an antibody or fragment thereof which specifically binds to at least one prostate tumor antigen, for a time and under conditions sufficient for the formation of antibody/antigen complexes, and detecting the complex containing the antibody. The antibody can be attached to a solid phase and either a monoclonal or polyclonal antibody. The antibody specifically binds to a polypeptide selected from the group consisting of SEQUENCE ID NOS 10–36, or fragments thereof.

Another method for detecting prostate tumor antibodies in a test sample suspected of containing said antibodies comprises contacting the test sample with a polypeptide wherein said polypeptide contains at least one prostate tumor epitope comprising an amino acid sequence or fragment thereof having at least 35% identity to an amino acid of prostate tumor, for a time and under conditions sufficient to allow antigen/antibody complexes to form and detecting said complexes which contain the polypeptide. The polypeptide can be attached to a solid phase. Further, the polypeptide can be a recombinant protein or a synthetic peptide which encodes at least one epitope of prostate tumor gene having at least 35% identity to an amino acid of prostate tumor gene provided herein.

The present invention provides a tissue culture grown cell containing a prostate tumor gene or a fragment thereof. Such prostate tumor gene is transfected into the cell.

A method for producing antibodies to prostate tumor gene comprising administering to an individual an isolated immunogenic polypeptide or fragment thereof comprising at least one prostate tumor epitope in an amount sufficient to produce an immune response, also is provided.

Diagnostic reagents comprise a polynucleotide of prostate tumor gene, wherein said polynucleotide or fragment thereof encodes at least one epitope of prostate tumor gene. The epitope has at least 35% identity to polynucleotide selected from the group consisting of SEQUENCE ID NOS 1 to 9. Another diagnostic reagent provided by the present invention comprises a polypeptide containing an epitope of prostate tumor gene provided herein or fragment thereof. The polypeptide is selected from the group consisting of SEQUENCE ID NO 10, SEQUENCE ID NO 11, SEQUENCE ID NO 12, SEQUENCE ID NO 13, SEQUENCE ID NO 14, SEQUENCE ID NO 15, SEQUENCE ID NO 16, SEQUENCE ID NO 17, SEQUENCE ID NO 18, SEQUENCE ID NO 19, SEQUENCE ID NO 20, SEQUENCE ID NO 21, SEQUENCE ID NO 22, SEQUENCE ID NO 23, SEQUENCE ID NO 24, SEQUENCE ID NO 25, SEQUENCE ID NO 26, SEQUENCE ID NO 27, SEQUENCE ID NO 28, SEQUENCE ID NO 29, SEQUENCE ID NO 30, SEQUENCE ID NO 31, SEQUENCE ID NO 32, SEQUENCE ID NO 33, SEQUENCE ID NO 34, SEQUENCE ID NO 35 and SEQUENCE ID NO 36, and fragments thereof.

BRIEF DESCRIPTION OF THE DRAWINGS

FIG. 1A-1–9 shows the nucleotide alignment of clones g885075 (SEQUENCE ID NO 1), 1512846 (SEQUENCE ID NO 2), 1699634 (SEQUENCE ID NO 3), 1444924 (SEQUENCE ID NO 4), 1209763 (SEQUENCE ID NO 5), 612079 (SEQUENCE ID NO 6), 608177 (SEQUENCE ID NO 7), and 842007 (SEQUENCE ID NO 8).

DETAILED DESCRIPTION OF THE INVENTION

Figure 1B:
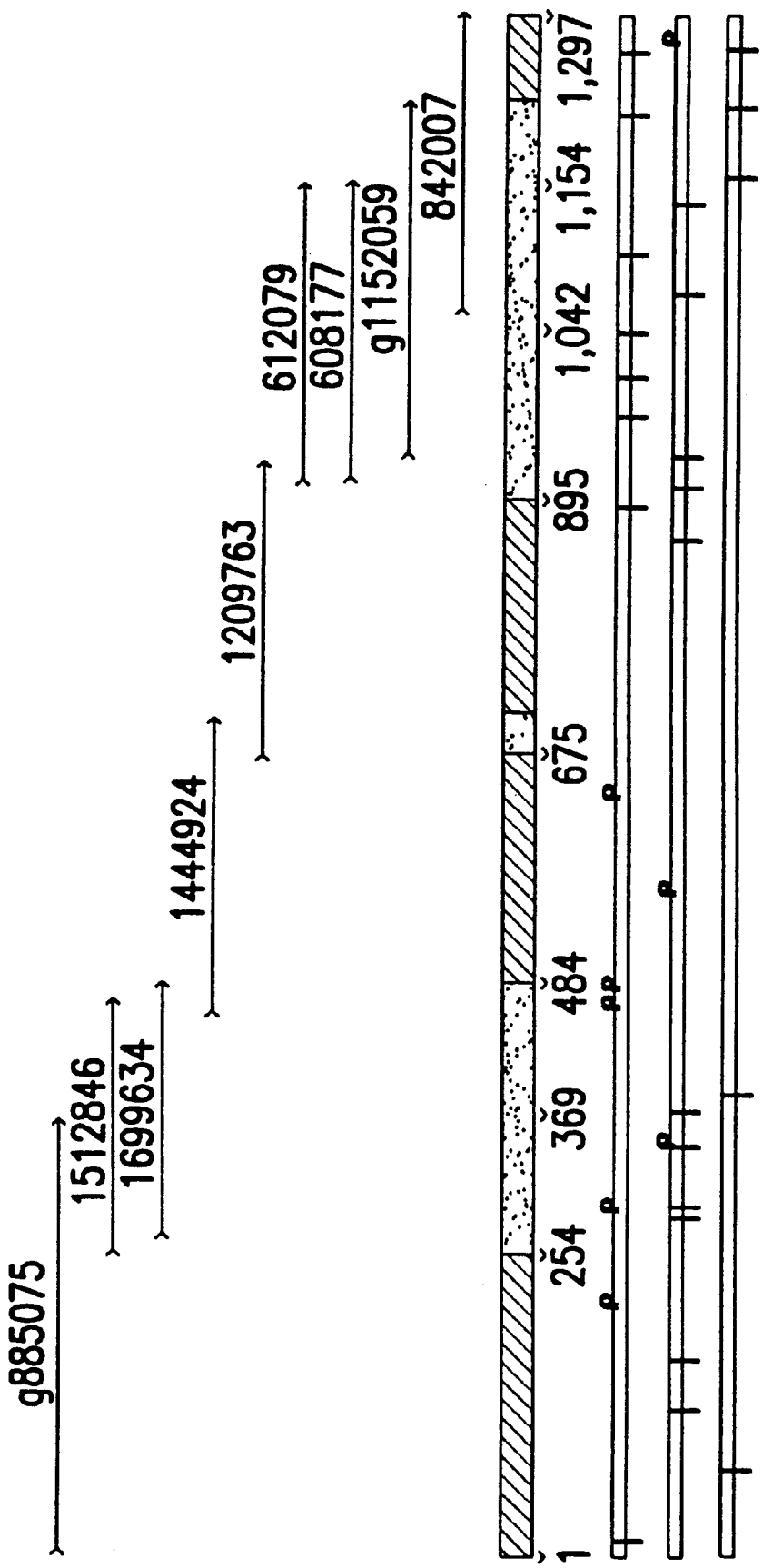
FIG. 1B shows the consensus nucleotide sequence (SEQUENCE ID NO 9) of the nucleotide alignment of clones g885075 (SEQUENCE ID NO 1), 1512846 (SEQUENCE ID NO 2), 1699634 (SEQUENCE ID NO 3), 1444924 (SEQUENCE ID NO 4), 1209763 (SEQUENCE ID NO 5), 612079 (SEQUENCE ID NO 6), 608177 (SEQUENCE ID NO 7), and 842007 (SEQUENCE ID NO 8).

The present invention provides methods for assaying a test sample for products of a prostate tumor gene, which comprises making cDNA from mRNA in the test sample, and detecting the cDNA as an indication of the presence of prostate tumor gene. The method may include an amplification step, wherein portions of the cDNA corresponding to the gene or fragment thereof is amplified. Methods also are provided for assaying for the translation products of mRNAs. Test samples which may be assayed by the methods provided herein include tissues, cells, body fluids and secretions. The present invention also provides reagents such as oligonucleotide primers and polypeptides which are useful in performing these methods.

Portions of the nucleic acid sequences disclosed herein are useful as primers for the reverse transcription of RNA or for the amplification of cDNA; or as probes to determine the presence of certain cDNA sequences in test samples. Also disclosed are nucleic acid sequences which permit the production of encoded polypeptide sequences which are useful as standards or reagents in diagnostic immunoassays, targets for pharmaceutical screening assays and/or as components or target sites for various therapies. Monoclonal and polyclonal antibodies directed against at least one epitope contained within these polypeptide sequences are useful for diagnostic tests as well as delivery agents for therapeutic agents and for screening for diseases or conditions associated with prostate tumor, especially prostate cancer. Isolation of sequences of other portions of the gene of interest can be accomplished by utilizing probes or PCR primers derived from these nucleic acid sequences, thus allowing additional probes and polypeptides of the genome of interest to be established, which also will be useful in the diagnosis, prognosis and/or treatment of diseases and conditions characterized by the prostate tumor gene disclosed herein.

The techniques for determining the amino acid sequence "similarity" are well-known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. The techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity." Two amino acid sequences likewise can be compared by determining their "percent identity." The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known in the art.

The compositions and methods described herein will enable the identification of certain markers as indicative of prostate tumor; the information obtained therefrom will aid in the diagnosis, staging, monitoring, prognosis and/or therapy of diseases or conditions associated with prostate tumor, especially prostate cancer. Test methods include, for example, probe assays which utilize the sequence(s) provided herein and which also may utilize nucleic acid amplification methods such as the polymerase chain reaction (PCR), the ligase chain reaction (LCR); and hybridization. In addition, the nucleotide seqluences provided herein contain open reading frames from which an immunogenic epitope may be found. This epitope is believed to be unique to the disease state or condition associated with prostate tumor gene. The uniqueness of the epitope may be determined by its immunological reactivity with the specific prostate tumor gene, especially cancer of the prostate, and lack of immunological reactivity with tissue(s) from nondiseased prostates. Methods for determining immunological reactivity are well-known and include but are not limited to, for example, radioimmunoassay (RIA), enzyme-linked immunosorbent assay (ELISA), hemagglutination (HA), fluorescence polarization immunoassay (FPIA); chemiluminescent immunoassay (CLIA), and others; several examples of suitable methods are described herein.

Unless otherwise stated, the following terms shall have the following meanings:

A polynucleotide "derived from" a designated sequence refers to a polynucleotide sequence which is comprised of a sequence of approximately at least about 6 nucleotides, is preferably at least about 8 nucleotides, is more preferably at least about 10–12 nucleotides, and even more preferably is at least about 15–20 nucleotides corresponding, i.e., identical to or complementary to, a region of the designated nucleotide sequence. The sequence may be complementary to or identical to a sequence which is unique to a particular polynucleotide sequence as determined by techniques known in the art. Comparisions to sequences in databanks, for example, can be used as a method to determine the uniqueness of a designated sequence. Regions from which sequences may be derived include but are not limited to regions encoding specific epitopes, as well as non-translated and/or non-transcribed regions.

The derived polynucleotide will not necessarily be derived physically from the nucleotide sequence of interest under study, but may be generated in any manner, including but not limited to chemical synthesis, replication, reverse transcription or transcription, which is based on the information provided by the sequence of bases in the region(s) from which the polynucleotide is derived; as such, it may represent either a sense or an antisense orientation of the original polynucleotide. In addition, combinations of regions corresponding to that of the designated sequence may be modified in ways known in the art to be consistent with an intended use.

The term "primer" denotes a specific oligonucleotide sequence complementary to a target nucleotide sequence and used to hybridize to the target nucleotide sequence and serve as an initiation point for nucleotide polymerization catalyzed by either DNA polymerase, RNA polymerase or reverse transcriptase.

The term "probe" denotes a defined nucleic acid segment (or nucleotide analog segment, i.e., PNA) which can be used to identify specific DNA present in samples bearing the complementary sequence.

A "polypeptide" or "amino acid" sequence derived from a designated nucleic acid sequence refers to a polypeptide having an amino acid sequence identical to that of a polypeptide encoded in the sequence or a portion thereof wherein the portion consists of at least 3 to 5 amino acids, and more preferably at least 8 to 10 amino acids, and even more preferably 15 to 20 amino acids, or which is immunologically identifiable with a polypeptide encoded in the sequence.

A "recombinant polypeptide" as used herein means at least a polypeptide which by virtue of its origin or manipulation is not associated with all or a portion of the polypeptide with which it is associated in nature and/or is linked to a polypeptide other than that to which it is linked in nature. A recombinant or derived polypeptide is not necessarily translated from a designated nucleic acid sequence. It also may be generated in any manner, including chemical synthesis or expression of a recombinant expression system.

The term "synthetic peptide" as used herein means a polymeric form of amino acids of any length, which may be chemically synthesized by methods well-known to the routineer. These synthetic peptides are useful in various applications.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as, double- and single-stranded RNA. It also includes modifications, such as methylation or capping, and unmodified forms of the polynucleotide.

"A sequence corresponding to a cDNA" means that the sequence contains a polynucleotide sequence that is identical to or complementary to a sequence in the designated DNA. The degree (or "percent") of identity or complementarity to the cDNA will be approximately 50% or greater, will preferably be at least about 70% or greater, and more preferably will be at least about 90%. The sequence that corresponds will be at least about 50 nucleotides in length, will preferably be about 60 nucleotides in length, and more preferably, will be at least about 70 nucleotides in length. The correspondence between the gene or gene fragment of interest and the cDNA can be determined by methods known in the art, and include, for example, a direct comparison of the sequenced material with the cDNAs described, or hybridization and digestion with single strand nucleases, followed by size determination of the digested fragments.

"Purified polynucleotide" refers to a polynucleotide of interest or fragment thereof which is essentially free, i.e., contains less than about 50%, preferably less than about 70%, and more preferably, less than about 90% of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density. Thus, "purified polypeptide" means a polypeptide of interest or fragment thereof which is essentially free, that is, contains less than about 50%, preferably less than about 70%, and more preferably, less than about 90% of cellular components with which the polypeptide of interest is naturally associated. Methods for purifying are known in the art.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Polypeptide" as used herein indicates a molecular chain of amino acids and does not refer to a specific length of the product. Thus, peptides, oligopeptides and proteins are included within the definition of polypeptide. This term, however, is not intended to refer to post-expression modifications of the polypeptide, for example, glycosylations, acetylations, phosphorylations and the like.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

As used herein "replicon" means any genetic element, such as a plasmid, a chromosome or a virus, that behaves as an autonomous unit of polynucleotide replication within a cell.

A "vector" is a replicon in which another polynucleotide segment is attached, such as to bring about the replication and/or expression of the attached segment.

The term "control sequence" refers to polynucleotide sequences which are necessary to effect the expression of coding sequences to which they are ligated. The nature of such control sequences differs depending upon the host organism. In prokaryotes, such control sequences generally include promoter, ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in and are unique to the designated polypeptide(s). Immunological identity may be determined by antibody binding and/or competition in binding. These techniques are known to the routineer and also are described herein. The uniqueness of an epitope also can be determined by computer searches of known data banks, such as GenBank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an epitope of interest" means naturally occurring polypeptides of interest or fragments thereof, as well as polypeptides prepared by other means, for example, by chemical synthesis or the expression of the polypeptide in a recombinant organism.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Treatment" refers to prophylaxis and/or therapy.

The term "individual" as used herein refers to vertebrates, particularly members of the mammalian species and includes but is not limited to domestic animals, sports animals, primates and humans; more particularly the term refers to humans.

The term "sense strand" or "plus strand" (or "+") as used herein denotes a nucleic acid that contains the sequence that encodes the polypeptide. The term "antisense strand" or "minus strand" (or "−") denotes a nucleic acid that contains a sequence that is complementary to that of the "plus" strand.

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitorurinary tracts, tears, saliva, milk, white blood cells, myelomas and the like; biological fluids such as cell culture supernatants; fixed tissue specimens; and fixed cell specimens.

"Purified product" refers to a preparation of the product which has been isolated from the cellular constituents with which the product is normally associated, and from other types of cells which may be present in the sample of interest.

"PNA" denotes a "peptide nucleic acid analog" which may be utilized in a procedure such as an assay described herein to determine the presence of a target. "MA" denotes a "morpholino analog" which may be utilized in a procedure such as an assay described herein to determine the presence of a target. See, for example, U.S. Pat. No. 5,378,841, which is incorporated herein by reference. PNAs are neutrally charged moieties which can be directed against RNA targets or DNA. PNA probes used in assays in place of, for example, the DNA probes of the present invention, offer advantages not achievable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with such signal generating compounds as fluorescein, radionucleotides, chemiluminescent compounds, and the like. PNAs or other nucleic acid analogs such as MAs thus can be used in assay methods in place of DNA or RNA. Although assays are described herein utilizing DNA probes, it is within the scope of the routineer that PNAs or MAs can be substituted for RNA or DNA with appropriate changes if and as needed in assay reagents.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a peptide, an amino acid, a nucleotide target, and the like.

An "Expressed Sequence Tag" or "EST" refers to the partial sequence of a cDNA insert which has been made by reverse transcription of mRNA extracted from a tissue, followed by insertion into a vector.

A "transcript image" refers to a table or list giving the quantitative distribution of ESTs in a library and represents the genes active in the tissue from which the library was made.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules.

The term "hapten," as used herein, refers to a partial antigen or non-protein binding member which is capable of binding to an antibody, but which is not capable of eliciting antibody formation unless coupled to a carrier protein.

A "capture reagent," as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") which is capable of generating and generates a measurable signal detectable by external means, conjugated ("attached") to a specific binding member. "Specific binding member" as used herein means a member of a specific binding pair. That is, two different molecules where one of the molecules through chemical or physical means specifically binds to the second molecule. In addition to being an antibody member of a specific binding pair, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazol or adamantane.

The various "signal-generating compounds" (labels) contemplated include chromogens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (red blood cells "fixed" by pyruvic aldehyde and formaldehyde, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the present invention that the solid phase also can comprise any suitable porous material with sufficient porosity to allow access by detection antibodies and a suitable surface affinity to bind antigens. Microporous structure generally are preferred, but materials with gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces. Other suitable solid supports are known in the art.

Reagents.

The present invention provides reagents such as polynucleotide sequences derived from a prostate tumor of interest, polypeptides encoded therein, and antibodies developed from these polypeptides. The present invention also provides reagents such as oligonucleotide fragments derived from the disclosed polynucleotides and nucleic acid sequences complementary to the these polynucleotides. The polynucleotides or polypeptides or antibodies of the present invention may be used in the diagnosis, prognosis, and/or treatment of individuals with conditions associated with prostate tumor gene, such as prostate cancer, or to identify a predisposition to this condition. The sequences disclosed herein represent unique polynucleotides which can be used in assays or for producing a prostate tumor specific profile of gene transcription activity.

Selected prostate tumor-derived polynucleotides can be used in the methods described herein for the detection of normal or altered gene expression. Such methods may employ the prostate tumor-derived polynucleotides disclosed herein or oligonucleotides, fragments or derivatives thereof, or nucleic acid sequences complementary to these polynucleotides.

The polynucleotides disclosed herein, their complementary sequences or fragments of either can be used in assays to detect, amplify or quantify genes, cDNAs or mRNAs relating prostate tumor and conditions associated with it. They also can be used to identify an entire or partial coding region which encodes for a prostate tumor polypeptide. They further can be provided in individual containers in the form of a kit for assays, or provided as individual compositions. If provided in a kit for assays, other suitable reagents such as buffers, conjugates and the like may be included.

The polynucleotide(s) may be in the form of mRNA or DNA. Polynucleotides in the form of DNA, cDNA, genomic DNA, and synthetic DNA are within the scope of the present invention. The DNA may be double-stranded or single-stranded, and if single stranded may be the coding (sense) strand or non-coding (anti-sense) strand. The coding sequence which encodes the polypeptide may be identical to the coding sequence provided herein or may be a different coding sequence which coding sequence, as a result of the redundancy or degeneracy of the genetic code, encodes the same polypeptide as the DNA provided herein.

This polynucleotide may include only the coding sequence for the polypeptide, or the coding sequence for the polypeptide and additional coding sequence such as a leader or secretory sequence or a proprotein sequence, or the coding sequence for the polypeptide (and optionally additional coding sequence) and non-coding sequence, such as a non-coding sequence 5' and/or 3' of the coding sequence for the polypeptide.

In addition, the invention includes variant polynucleotides containing modifications such as polynucleotide deletions, substitutions or additions; and any polypeptide modification resulting from the variant polynucleotide sequence. A polynucleotide of the present invention also may have a coding sequence which is a naturally occurring allelic variant of the coding sequence provided herein.

In addition, the coding sequence for the polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the form of the polypeptide. The polynucleotides may also encode for a proprotein which is the protein plus additional 5' amino acid residues. A protein having a prosequence is a proprotein and may in some cases be an inactive form of the protein. Once the prosequence is cleaved an active protein remains. Thus, the polynucleotide of the present invention may encode for a protein, or for a protein having a prosequence or for a protein having both a presequence (leader sequence) and a prosequence.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein. See, for example, I. Wilson, et al., *Cell* 37: 767 (1984).

It is contemplated that polynucleotides will be considered to hybridize to the sequences provided herein if there is at least 50%, and preferably at least 70%, identity between the polynucleotide and the sequence.

The present invention also provides an antibody produced by using a purified prostate tumor gene polypeptide of which at least a portion of the polypeptide is encoded by prostate tumor gene polynucleotide selected from the polynucleotides provided herein. These antibodies may be used in the methods provided herein for the detection of prostate tumor polypeptides in test samples. The antibody also may be used for therapeutic purposes, for example, in neutralizing the activity of a prostate tumor polypeptide in conditions associated with altered or abnormal expression of prostate tumor.

The present invention further relates to a prostate tumor polypeptide which has the deduced amino acid sequence as provided herein, as well as fragments, analogs and derivatives of such polypeptide. The polypeptide of the present invention may be a recombinant polypeptide, a natural purified polypeptide or a synthetic polypeptide. The fragment, derivative or analog of the prostate tumor polypeptide may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence which is employed for purification of the polypeptide or a proprotein sequence. Such fragments, derivatives and analogs are within the scope of the present invention. The polypeptides and polynucleotides of the present invention are preferably provided in an isolated form, and preferably purified.

Thus, a polypeptide of the present invention may have an amino acid sequence that is identical to that of the naturally occurring polypeptide or that is different by minor variations due to one or more amino acid substitutions. The variation may be a "conservative change" typically in the range of about 1 to 5 amino acids, wherein the substituted amino acid has similar structural or chemical properties, eg, replacement of leucine with isoleucine or threonine with serine. In contrast, variations may include nonconservative changes, eg, replacement of a glycine with a tryptophan. Similar minor variations may also include amino acid deletions or insertions, or both. Guidance in determining which and how many amino acid residues may be substituted, inserted or deleted without changing biological or immunological activity may be found using computer programs well known in the art, for example, DNASTAR software (DNASTAR Inc., Madison Wis.).

Probes constructed according to the polynucleotide sequences of the present invention can be used in various assay methods to provide various types of analysis. For example, such probes can be used in Fluorescent In Situ Hybridization (FISH) technology to perform chromosomal analysis, and used to identify cancer-specific structural alterations in the chromosomes, such as deletions or translocations that are visible from chromosome spreads or detectable using PCR-generated and/or allele specific oligonulcleotides probes, allele specific amplification or by direct sequencing. Probes also can be labeled with radioisotopes, directly- or indirectly- detectable haptens, or fluorescent molecules, and utilized for in situ hybridization studies to evaluate the mRNA expression of the gene comprising the polynucleotide in fixed tissue specimens or cells.

This invention also provides teachings as to the production of the polynucleotides and polypeptides provided herein.

Probe Assays

The sequences provided herein may be used to produce probes which can be used in assays for the detection of nucleic acids in test samples. The probes may be designed from conserved nucleotide regions of the polynucleotides of interest or from non-conserved nucleotide regions of the polynucleotide of interest. The design of such probes for optimization in assays is within the skill of the routineer. Generally, nucleic acid probes are developed from non-conserved or unique regions when maximum specificity is desired, and nucleic acid probes are developed from conserved regions when assaying for nucleotide regions that are closely related to, for example, different members of a multigene family or in related species like mouse and man.

The polymerase chain reaction (PCR) is a technique for amplifying a desired nucleic acid sequence (target) contained in a nucleic acid or mixture thereof. In PCR, a pair of primers are employed in excess to hybridize at the outside ends of complementary strands of the target nucleic acid. The primers are each extended by a polymerase using the target nucleic acid as a template. The extension products become target sequences themselves, following dissociation from the original target strand. New primers then are hybridized and extended by a polymerase, and the cycle is repeated to geometrically increase the number of target sequence molecules. PCR is disclosed in U.S. Pat. Nos. 4,683,195 and 4,683,202, which are incorporated herein by reference.

The Ligase Chain Reaction (LCR) is an alternate method for nucleic acid amplification. In LCR, probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3'hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EP-A-320 308 to K. Backman published Jun. 16, 1989 and EP-A-439 182 to K. Backman et al, published Jul. 31, 1991, both of which are incorporated herein by reference.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, which is incorporated herein by reference; or reverse transcribe mRNA into cDNA followed by asymmetric gap ligase chain reaction (RT-AGLCR) as described by R. L. Marshall, et al., *PCR Methods and Applications* 4: 80–84 (1994), which also is incorporated herein by reference.

Other known amplification methods which can be utilized herein include but are not limited to the so-called "NASBA" or "3SR" technique described in *PNAS USA* 87: 1874–1878 (1990) and also described in *Nature* 350 (No. 6313): 91–92 (1991); Q-beta amplification as described in published European Patent Application (EPA) No. 4544610; strand displacement amplification (as described in G. T. Walker et al., *Clin. Chem.* 42: 9–13 [1996]) and European Patent Application No. 684315; and target mediated amplification, as described by PCT Publication WO 9322461.

In one embodiment, the present invention generally comprises the steps of contacting a test sample suspected of containing a target polynucleotide sequence with amplification reaction reagents comprising an amplification primer, and a detection probe that can hybridize with an internal region of the amplicon sequences. Probes and primers employed according to the method herein provided are labeled with capture and detection labels wherein probes are labeled with one type of label and primers are labeled with the other type of label. Additionally, the primers and probes are selected such that the probe sequence has a lower melt temperature than the primer sequences. The amplification reagents, detection reagents and test sample are placed under amplification conditions whereby, in the presence of target sequence, copies of the target sequence (an amplicon) are produced. In the usual case, the amplicon is double stranded because primers are provided to amplify a target sequence and its complementary strand. The double stranded amplicon then is thermally denatured to produce single stranded amplicon members. Upon formation of the single stranded amplicon members, the mixture is cooled to allow the formation of complexes between the probes and single stranded amplicon members.

As the single stranded amplicon sequences and probe sequences were cooled, the probe sequences preferentially bound the single stranded amplicon members. This finding is counterintuitive given that the probe sequences are generally selected to be shorter than the primer sequences and therefore have a lower melt temperature than the primers. Accordingly, the melt temperature of the amplicon produced by the primers should also have a higher melt temperature than the probes. Thus, as the mixture was cooled, the re-formation of the double stranded amplicon would be expected. As previously stated, however, this is not the case. The probes were found to preferentially bind the single stranded amplicon members. Moreover, this preference of probe/single stranded amplicon binding exists even when the primer sequences are added in excess of the probes.

After the probe/single stranded amplicon member hybrids are formed, they are detected. Standard heterogeneous assay formats are suitable for detecting the hybrids using the detection labels and capture labels present on the primers and probes. The hybrids can be bound to a solid phase reagent by virtue of the capture label and detected by virtue of the detection label. In cases where the detection label is directly detectable, the presence of the hybrids on the solid phase can be detected by causing the label to produce a detectable signal, if necessary, and detecting the signal. In cases where the label is not directly detectable, the captured hybrids can be contacted with a conjugate, which generally comprises a binding member attached to a directly detectable label. The conjugate becomes bound to the complexes and the conjugates presence on the complexes can be detected with the directly detectable label. Thus, the presence of the hybrids on the solid phase reagent can be determined. Those skilled in the art will recognize that wash steps may be employed to wash away unhybridized amplicon or probe as well as unbound conjugate.

A test sample is typically anything suspected of containing a target sequence. Test samples can be prepared using methodologies well known in the art such as by obtaining a specimen from an individual and, if necessary, disrupting any cells contained therein to release target nucleic acids. Although the target sequence is described as single stranded, it also is contemplated to include the case where the target sequence is actually double stranded but is merely separated from its complement prior to hybridization with the amplification primer sequences. In the case where PCR is employed in this method, the ends of the target sequences are usually known. In cases where LCR or a modification thereof is employed in the preferred method, the entire target sequence is usually known. Typically, the target sequence is a nucleic acid sequence such as, for example, RNA or DNA.

The method provided herein can be used in well known amplification reactions that include thermal cycle reaction mixtures, particularly in PCR and GLCR. Amplification reactions typically employ primers to repeatedly generate copies of a target nucleic acid sequence, which target sequence is usually a small region of a much larger nucleic acid sequence. Primers are themselves nucleic acid sequences that are complementary to regions of a target sequence. Under amplification conditions, these primers hybridize or bind to the complementary regions of the target sequence. Copies of the target sequence typically are generated by the process of primer extension and/or ligation which utilizes enzymes with polymerase or ligase activity, separately or in combination, to add nucleotides to the hybridized primers and/or ligate adjacent probe pairs. The nucleotides that are added to the primers or probes, as monomers or preformed oligomers, are also complementary to the target sequence. Once the primers or probes have been sufficiently extended and/or ligated they are separated from the target sequence, for example, by heating the reaction mixture to a "melt temperature" which is one in which complementary nucleic acid strands dissociate. Thus, a sequence complementary to the target sequence is formed.

A new amplification cycle then can take place to further amplify the number of target sequences by separating any double stranded sequences, allowing primers or probes to hybridize to their respective targets, extending and/or ligating the hybridized primers or probes and re-separating. The complementary sequences that are generated by amplification cycles can serve as templates for primer extension or filling the gap of two probes to further amplify the number of target sequences. Typically, a reaction mixture is cycled between 20 and 100 times, more typically, a reaction mixture is cycled between 25 and 50 times. The numbers of cycles can be determined by the routineer. In this manner, multiple copies of the target sequence and its complementary sequence are produced. Thus, primers initiate amplification of the target sequence when it is present under amplification conditions.

Generally, two primers which are complementary to a portion of a target strand and its complement are employed in PCR. For LCR, four probes, two of which are complementary to a target sequence and two of which are similarly complementary to the targets complement, are generally employed. In addition to the primer sets and enzymes previously mentioned, a nucleic acid amplification reaction mixture may also comprise other reagents which are well known and include but are not limited to: enzyme cofactors such as manganese; magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

While the amplification primers initiate amplification of the target sequence, the detection (or hybridization) probe is not involved in amplification. Detection probes are generally nucleic acid sequences or uncharged nucleic acid analogs such as, for example, peptide nucleic acids which are disclosed in International Patent Application WO 92/20702; morpholino analogs which are described in U.S. Pat. Nos 5,185,444, 5,034,506, and 5,142,047; and the like. Depending upon the type of label carried by the probe, the probe is employed to capture or detect the amplicon generated by the amplification reaction. The probe is not involved in amplification of the target sequence and therefore may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified. U.S. patent application Ser. No. 07/049,061 filed Apr. 19, 1993 and incorporated herein by reference describes modifications which can be used to render a probe non-extendable.

Accordingly, the ratio of primers to probes is not important. Thus, either the probes or primers can be added to the reaction mixture in excess whereby the concentration of one would be greater than the concentration of the other. Alternatively, primers and probes can be employed in equivalent concentrations. Preferably, however, the primers are added to the reaction mixture in excess of the probes. Thus, primer to probe ratios of, for example, 5:1 and 20:1 are preferred.

While the length of the primers and probes can vary, the probe sequences are selected such that they have a lower melt temperature than the primer sequences. Hence, the primer sequences are generally longer than the probe sequences. Typically, the primer sequences are in the range of between 20 and 50 nucleotides long, more typically in the range of between 20 and 30 nucleotides long. The typical probe is in the range of between 10 and 25 nucleotides long.

Various methods for synthesizing primers and probes are well known in the art. Similarly, methods for attaching labels to primers or probes are also well known in the art. For example, it is a matter of routine to synthesize desired nucleic acid primers or probes using conventional nucleotide phosphoramidite chemistry and instruments available from Applied Biosystems, Inc., (Foster City, Calif.), Dupont (Wilmington, Del.), or Milligen (Bedford Mass.). Many methods have been described for labeling oligonucleotides such as the primers or probes of the present invention. Enzo Biochemical (New York, N.Y.) and Clontech (Palo Alto, Calif.) both have described and commercialized probe labeling techniques. For example, a primary amine can be attached to a 3' oligo terminus using 3'-Amine-ON CPG™ (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, copending applications U.S. Ser. Nos. 625,566, filed Dec. 11, 1990 and 630,908, filed Dec. 20, 1990, which are each incorporated herein by reference, teach methods for labeling probes at their 5' and 3' termini, respectively. Publications WO 92/10505, published Jun. 25, 1992 and WO 92/11388 published Jul. 9, 1992 teach methods for labeling probes at their 5' and 3' ends, respectively. According to one known method for labeling an oligonucleotide, a label-phosphoramidite reagent is prepared and used to add the label to the oligonucleotide during its synthesis. See, for example, N. T. Thuong et al., *Tet. Letters* 29(46): 5905–5908 (1988); or J. S. Cohen et al., published U.S. patent application Ser. No. 07/246,688 (NTIS ORDER No. PAT-APPL-7-246,688) (1989). Preferably, probes are labeled at their 3' and 5' ends.

Capture labels are carried by the primers or probes and can be a specific binding member which forms a binding pair with the solid phase reagent's specific binding member. It will be understood, of course that the primer or probe itself may serve as the capture label. For example, in the case where a solid phase reagent's binding member is a nucleic acid sequence, it may be selected such that it binds a complementary portion of the primer or probe to thereby immobilize the primer or probe to the solid phase. In cases where the probe itself serves as the binding member, those skilled in the art will recognize that the probe will contain a sequence or "tail" that is not complementary to the single stranded amplicon members. In the case where the primer itself serves as the capture label, at least a portion of the primer will be free to hybridize with a nucleic acid on a solid phase because the probe is selected such that it is not fully complementary to the primer sequence.

Generally, probe/single stranded amplicon member complexes can be detected using techniques commonly employed to perform heterogeneous immunoassays. Preferably, in this embodiment, detection is performed according to the protocols used by the commercially available Abbott LCx® instrumentation (Abbott Laboratories, Abbott Park, Ill.).

The primers and probes disclosed herein are useful in typical PCR assays, wherein the test sample is contacted with a pair of primers, amplification is performed, the hybridization probe is added, and detection is performed.

Another method provided by the present invention comprises contacting a test sample with a plurality of polynucleotides wherein at least one polynucleotide is provided herein, hybridizing the test sample with the plurality of polynucleotides and detecting the hybridization complexes. The hybridization complexes are identified and quantitated to compile a profile which is indicative prostate tumor. Expressed RNA sequences may further be detected by reverse transcription and amplification of the DNA product by procedures well-known in the art, including polymerase chain reaction (PCR).

Drug Screening and Gene Therapy.

The present invention also encompasses the use of gene therapy methods for the introduction of anti-sense prostate tumor gene derived molecules such as polynucleotides or oligonucleotides of the present invention into patients with conditions associated with abnormal expression of polynucleotides related to prostate tumor including cancer, especially prostate cancer. These molecules, including antisense RNA and DNA fragments and ribozymes, are designed to inhibit the translation of a prostate tumor derived polynucleotide mRNA, and may be used therapeutically in the treatment of conditions associated with altered or abnormal expression of a prostate tumor derived polynucleotide.

Alternatively, the oligonucleotides described above can be delivered to cells by procedures in the art such that the anti-sense RNA or DNA may be expressed in vivo to inhibit production of prostate tumor derived polypeptide in the manner described above. Antisense constructs to prostate tumor derived polynucleotide, therefore, reverse the action of prostate tumor derived transcripts and may be used for treating prostate tumor conditions such as prostate cancer. These antisense constructs may also be used to treat tumor metastases.

The present invention also provides a method of screening a plurality of compounds for specific binding to an prostate tumor derived polypeptide, or any fragment thereof, to identify at least one compound which specifically binds the prostate tumor derived polypeptide. Such a method comprises the steps of providing at least one compound; combining the prostate tumor derived polypeptide with each compound under suitable conditions for a time sufficient to allow binding; and detecting prostate tumor polypeptide binding to each compound.

Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription, thereby preventing transcription and the production of prostate tumor derived polypeptide. For triple helix, see, for example, Lee et al, *Nucl. Acids Res.* 6: 3073 (1979); Cooney et al, *Science* 241: 456 (1988); and Dervan et al, *Science* 251: 1360 (1991) The antisense RNA oligonucleotide hybridizes to the mRNA in vivo and blocks translation of an mRNA molecule into the prostate tumor derived polypeptide. For antisense, see, for example, Okano, *J. Neurochem.* 56: 560 (1991); and "Oligodeoxynucleotides as Antisense Inhibitors of Gene Expression", CRC Press, Boca Raton, Fla. (1988). Antisense oligonucleotides act with greater efficacy when modified to contain artificial internucleotide linkages which render the molecule resistant to nuclcolytic cleavage. Such artificial internucleotide linkages include but are not limited to methylphosphonate, phosphorothiolate and phosphoroamydate internucleotide linkages.

The polypeptide or peptide fragment employed in such a test may either be free in solution, affixed to a solid support, borne on a cell surface or located intracellularly. One method of drug screening utilizes eukaryotic or prokaryotic host cells which are stably transformed with recombinant nucleic acids which can express the polypeptide or peptide fragment. Drugs may be screened against such transformed cells in competitive binding assays. For example, the formation of complexes between a polypeptide and the agent being tested can be measured in either viable or fixed cells.

The present invention thus provides methods of screening for drugs or any other agent which can be used to treat diseases associated with prostate tumor. These methods comprise contacting the drug with a polypeptide or fragment thereof and assaying for either the presence of a complex between the agent and the polypeptide, or for the presence of a complex between the polypeptide and the cell. In competitive binding assays, the polypeptide typically is labeled. After suitable incubation, free (or uncomplexed) polypeptide or fragment thereof is separated from that present in bound form, and the amount of free or uncomplexed label is a measure of the ability of the particular drug to bind to polypeptide or to interfere with the polypeptide/cell complex.

The present invention also encompasses the use of competitive drug screening assays in which neutralizing antibodies capable of binding polypeptide specifically compete with a test drug for binding to the polypeptide or fragment thereof. In this manner, the antibodies can be used to detect the presence of any polypeptide in the test sample which shares one or more antigenic determinants with a polypeptide provided herein.

Another technique for drug screening provides high throughput screening for compounds having suitable binding affinity to at least one polypeptide disclosed herein. Briefly, large numbers of different small peptide test compounds are synthesized on a solid phasee, such as plastic pins or some other surface. The peptide test compounds are reacted with polypeptide and washed. Polypeptide thus bound to the solid phase is detected by methods well-known in the art. Purified polypeptide can also be coated directly onto plates for use in the drug screening techniques described herein. In addition, non-neutralizing antibodies can be used to capture the polypeptide and immobilize it on the solid support. See, for example, EP 84/03564, published on Sept. 13, 1984, which is incorporated herein by reference.

The goal of rational drug design is to produce structural analogs of biologically active polypeptides of interest or of the small molecules including agonists, antagonists, or inhibitors with which they interact. Such structural analogs can be used to fashion drugs which are more active or stable forms of the polypeptide or which enhance or interfere with the function of a polypeptide in vivo. J. Hodgson, *Bio/Technology* 9: 19–21 (1991), incorporated herein by reference.

For example, in one approach, the three-dimensional structure of a polypeptide, or of a polypeptide-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous polypeptide-like molecules or to identify efficient inhibitors.

Useful examples of rational drug design may include molecules which have improved activity or stability as shown by S. Braxton et al., *Biochemistry* 31: 7796–7801 (1992), or which act as inhibitors, agonists, or antagonists of native peptides as shown by S. B. P. Athauda et al., *J Biochem.* (*Tokyo*) 113 (6): 742–746 (1993), incorporated herein by reference.

It also is possible to isolate a target-specific antibody, selected by an assay as described hereinabove, and then to determine its crystal structure. In principle this approach yields a pharmacophore upon which subsequent drug design can be based. It further is possible to bypass protein crystallography altogether by generating anti-idiotypic antibodies ("anti-ids") to a functional, pharmacologically active antibody. As a mirror image of a mirror image, the binding site of the anti-id is an analog of the original receptor. The anti-id then could be used to identify and isolate peptides from banks of chemically or biologically produced peptides. The isolated peptides then can act as the pharmacophore (that is, a prototype pharmaceutical drug).

A sufficient amount of a recombinant polypeptide of the present invention may be made available to perform analytical studies such as X-ray crystallography. In addition, knowledge of the polypeptide amino acid sequence which are derivable from the nucleic acid sequence provided herein will provide guidance to those employing computer modeling techniques in place of or in addition to x-ray crystallography.

Antibodies specific to the prostate tumor derived polypeptide may further be used to inhibit the biological action of the polypeptide by binding to the polypeptide. In this manner, the antibodies may be used in therapy, for example, to treat prostate tumor including prostate cancer and its metastases.

Further, such antibodies can detect the presence or absence of prostate tumor derived polypeptide and, therefore, are useful as diagnostic markers for the diagnosis of prostate tumor, especially prostate cancer. Such antibodies may also function as a diagnostic marker for prostate tumor conditions such as prostate cancer. The present invention also is directed to antagonists and inhibitors of the polypeptides of the present invention. The antagonists and inhibitors are those which inhibit or eliminate the function of the polypeptide. Thus, for example, an antagonist may bind to a polypeptide of the present invention and inhibit or eliminate its function. The antagonist, for example, could be an antibody against the polypeptide which eliminates the activity of prostate tumor derived polypeptide by binding to prostate tumor derived polypeptide, or in some cases the antagonist may be an oligonucleotide. Examples of small molecule inhibitors include but are not limited to small peptides or peptide-like molecules.

The antagonists and inhibitors may be employed as a composition with a pharmaceutically acceptable carrier, including but not limited to saline, buffered saline, dextrose, water, glycerol, ethanol and combinations thereof. Administration of prostate tumor derived polypeptide inhibitors are preferably systemic. The present invention also provides an antibody which inhibits the action of such polypeptide.

Recombinant Technology.

The present invention provides host cells and expression vectors comprising polynucleotides of the present invention and methods for the production of polypeptides they encode. Such methods comprise culturing the host cells under conditions suitable for the expression of the prostate tumor derived polynucleotide and recovering the prostate tumor derived polypeptide from the cell culture.

The present invention also provides vectors which include polynucleotides of the present invention, host cells which are genetically engineered with vectors of the present invention and the production of polypeptides of the present invention by recombinant techniques.

Host cells are genetically engineered (transduced or transformed or transfected) with the vectors of this invention which may be a cloning vector or an expression vector. The vector may be in the form of a plasmid, a viral particle, a phage, etc. The engineered host cells can be cultured in conventional nutrient media modified as appropriate for activating promoters, selecting transformants or amplifying the prostate tumor derived genes. The culture conditions, such as temperature, pH and the like, are those previously used with the host cell selected for expression, and will be apparent to the ordinarily skilled artisan.

The polynucleotide of the present invention may be employed for producing a polypeptide by recombinant techniques. Thus, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used so long as it is replicable and viable in the host.

The appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art. The DNA sequence in the expression vector is operatively linked to an appropriate expression control sequence(s) (promoter) to direct mRNA synthesis. Representative examples of such promoters include but are not limited to LTR or SV40 promoter, the E. coli lac or trp, the phage lambda P sub L promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, the expression vectors preferably contain a gene to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as E. coli, Salmonella typhimurium; Streptomyces sp.; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings provided herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pSPORT1 (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, SP6, T7, gpt, lambda P sub R, P sub L and trp. Eukaryotic promoters include cytomegalovirus (CMV) immediate early, herpes simplex virus (HSV) thymidine kinase, early and late SV40, LTRs from retrovirus, and mouse metallothionein-I. Selection of the appropriate vector and promoter is well within the level of ordinary skill in the art.

In a further embodiment, the present invention provides host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (L. Davis et al., "Basic Methods in Molecular Biology", 2nd edition, Appleton and Lang, Paramount Publishing, East Norwalk, Conn. (1994).

The constructs in host cells can be used in a conventional manner to produce the gene product encoded by the recombinant sequence. Alternatively, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual*, Second Edition, (Cold Spring Harbor, N.Y., 1989), which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a routine matter of choice.

Useful expression vectors for bacterial use comprise a selectable marker and bacterial origin of replication derived from plasmids comprising genetic elements of the well-known cloning vector pBR322 (ATCC 37017). Other vectors include but are not limited to PKK223-3 (Pharmacia Fine Chemicals, Uppsala, Sweden) and GEM1 (Promega Biotec, Madison, Wis.). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction), and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well-known to the ordinary artisan.

Various mammalian cell culture systems can also be employed to express recombinant protein. Examples of mammalian expression systems include the COS-7 lines of monkey kidney fibroblasts described by Gluzman, *Cell* 23: 175 (1981), and other cell lines capable of expressing a compatible vector, such as the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Representative, useful vectors include pRc/CMV and pcDNA3 (available from Invitrogen, San Diego, Calif.).

Prostate tumor polypeptide is recovered and purified from recombinant cell cultures by known methods including ammonium sulfate or ethanol precipitation, acid extraction, anion or cation exchange chromatography, phosphocellulose chromatography, hydrophobic interaction chromatography, hydroxyapatite chromatography or lectin chromatography. It is preferred to have low concentrations (approximately 0.1–5 mM) of calcium ion present during purification (Price, et al., *J. Biol. Chem.* 244: 917 [1969]). Protein refolding steps can be used, as necessary, in completing configuration of the protein. Finally, high performance liquid chromatography (HPLC) can be employed for final purification steps.

The polypeptides of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. The polypeptides of the invention may also include an initial methionine amino acid residue.

The starting plasmids can be constructed from available plasmids in accord with published, known procedures. In addition, equivalent plasmids to those described are known in the art and will be apparent to the ordinarily skilled artisan.

The following is the general procedure for the isolation and analysis of cDNA clones. In a particular embodiment disclosed herein, mRNA was isolated from a prostate tumor diseased tissue characterized as a human prostate tumor and used to generate the cDNA library. Prostate tumor tissue was obtained by retropubic prostatectomy.

The cDNA inserts from random isolates of the prostate tumor library were sequenced in part, analyzed in detail set forth in the Examples and are disclosed in the Sequence Listing as SEQUENCE ID NOS 1–8, an d the consensus sequence of these inserts is presented as SEQUENCE ID NO 9. These polynucleotides may contain an entire open reading frame with or without associated regulatory sequences for a particular gene, or they may encode only a portion of the gene of interest. This is attributed to the fact that many genes are several hundred, and sometimes several thousand, bases in length and, with current technology, cannot be cloned in their entirety because of vector limitations, incomplete reverse transcription of the first strand, or incomplete replication of the second strand. Contiguous, secondary clones containing additional nucleotide sequence may be obtained using a variety of methods known to those of skill in the art.

Methods for DNA sequencing are well known in the art. Conventional enzymatic methods employ DNA polymerase, Klenow fragment, Sequenase (U.S. Biochemical Corp, Cleveland, Ohio) or Taq polymerase to extend DNA chains from an oligonucleotide primer annealed to the DNA template of interest. Methods have been developed for the use of both single-stranded and double-stranded templates. The chain termination reaction products may be electrophoresed on urea/polyacrylamide gels and detected either by autoradiography (for radionucleotide labeled precursors) or by fluorescence (for fluorescent-labeled precursors). Recent improvements in mechanized reaction preparation, sequencing and analysis using the fluorescent detection method have permitted expansion in the number of sequences that can be determined per day using machines such as the Applied Biosystems 377 DNA Sequencers (Applied Biosystems, Foster City, Calif.).

The reading frame of the nucleotide sequence can be ascertained by several types of analyses. First, reading frames contained within the coding sequence can be analyzed for the presence of start codon ATG and stop codons TGA, TAA or TAG. Typically, one reading frame will continue throughout the major portion of a cDNA sequence while the other two reading frames tend to contain numerous stop codons. In such cases reading frame determination is straightforward. In other more difficult cases, further analysis is required.

Algorithms have been created to analyze the occurrence of individual nucleotide bases at each putative codon triplet. See, for example J. W. Fickett, *Nuc Acids Res* 10: 5303 (1982). Coding DNA for particular organisms (bacteria, plants, and animals) tends to contain certain nucleotides within certain triplet periodicities, such as a significant preference for pyrimidines in the third codon position. These preferences have been incorporated into widely available software which can be used to determine coding potential (and frame) of a given stretch of DNA. The algorithm-derived information combined with start/stop codon information can be used to determine proper frame with a high degree of certainty. This, in turn, readily permits cloning of the sequence in the correct reading frame into appropriate expression vectors.

The nucleic acid sequences disclosed herein may be joined to a variety of other polynucleotide sequences and vectors of interest by means of well established recombinant DNA techniques. See J. Sambrook et al., supra. Vectors of interest include cloning vectors, such as plasmids, cosmids, phage derivatives, phagemids, as well as sequencing, replication, and expression vectors, and the like. In general, such vectors contain an origin of replication functional in at least one organism, convenient restriction endonuclease digestion sites, and selectable markers appropriate for particular host cells. The vectors can be transferred by a variety of means known to those of skill in the art into suitable host cells which then produce the desired DNA, RNA or polypeptides.

Occasionally, sequencing or random reverse transcription errors will mask the presence of the appropriate open reading frame or regulatory element. In such cases, it is possible to determine the correct reading frame by attempting to express the polypeptide and determining the amino acid sequence by standard peptide mapping and sequencing techniques. See, F. M. Ausubel, et al., *Current Protocols in Molecular Biology*, John Wiley & Sons, New York, N.Y. (1989). Additionally, the actual reading frame of a given nucleotide sequence may be determined by transfection of host cells with vectors containing all three potential reading frames. Only those cells with the nucleotide sequence in the correct reading frame will produce a peptide of the predicted length.

The nucleotide sequences provided herein have been prepared by current, state-of-the-art, automated methods and as such may contain unidentified nucleotides. These will not present a problem to those skilled in the art who wish to practice the invention. Several methods employing standard recombinant techniques, described in J. Sambrook (supra) or periodic updates thereof, may be used to complete the missing sequence information. The same techniques used for obtaining a full length sequence, as described herein, may be used to obtain nucleotide sequence.

Expression of a particular cDNA may be accomplished by subcloning the cDNA into an appropriate expression vector and transfecting this vector into an appropriate expression host. The cloning vector used for the generation of the prostate tumor cDNA library can be used for transcribing mRNA of a particular cDNA and contains a promoter for beta-galactosidase, an amino-terminal met and the subsequent seven amino acid residues of beta-galactosidase. Immediately following these eight residues is an engineered bacteriophage promoter useful for artificial priming and transcription and a number of unique restriction sites, including EcoR I, for cloning. The vector can be transfected into an appropriate host strain of *E. coli*.

Induction of the isolated bacterial strain with isopropylthiogalactoside (IPTG) using standard methods will produce a fusion protein which contains the first seven residues of beta-galactosidase, about 15 residues of linker, and the peptide encoded within the cDNA. Since cDNA clone inserts are generated by an essentially random process, there is one chance in three that the included cDNA will lie in the correct frame for proper translation. If the cDNA is not in the proper reading frame, the correct frame can be obtained by deletion or insertion of an appropriate number of bases by well known methods including in vitro mutagenesis, digestion with exonuclease 1II or mung bean nuclease, or oligonucleotide linker inclusion.

The cDNA can be shuttled into other vectors known to be useful for expression of protein in specific hosts. Oligonucleotide primers containing cloning sites and segments of DNA sufficient to hybridize to stretches at both ends of the target cDNA can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to, mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the beta-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require the addition of 3' poly A tail if the sequence of interest lacks poly A.

Additionally, the vector may contain promoters or enhancers which increase gene expression. Such promoters are host specific and include but are not limited to MMTV, SV40, or metallothionine promoters for CHO cells; trp, lac, tac or T7 promoters for bacterial hosts; or alpha factor, alcohol oxidase or PGH promoters for yeast. Adenoviral vectors with or without transcription enhancers, such as the rous sarcoma virus (RSV) enhancer, may be used to drive protein expression in mammalian cell lines. Once homogeneous cultures of recombinant cells are obtained, large quantities of recombinantly produced protein can be recovered from the conditioned medium and analyzed using chromatographic methods well known in the art. An alternative method for the production of large amounts of secreted protein involves the transformation of mammalian embryos and the recovery of the recombinant protein from milk produced by transgenic cows, goats, sheep, etc. Polypeptides and closely related molecules may be expressed recombinantly in such a way as to facilitate protein purification. One approach involves expression of a chimeric protein which includes one or more additional polypeptide domains not naturally present on human polypeptides. Such purification-facilitating domains include, but are not limited to, metal-chelating peptides such as histidine-tryptophan domains that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase from Invitrogen (San Diego, Calif.) between the polypeptide sequence and the purification domain may be useful for recovering the polypeptide.

Immunoassays.

The polypeptides including their fragments or derivatives or analogs thereof of the present invention, or cells expressing them, can be in a variety of assays, many of which are described herein, for the detection of antibodies to prostate tumor. They also can be used as an immunogen to produce antibodies. These antibodies can be, for example, polyclonal or monoclonal antibodies, chimeric, single chain and humanized antibodies, as well as Fab fragments, or the product of an Fab expression library. Various procedures known in the art may be used for the production of such antibodies and fragments.

For example, antibodies generated against a polypeptide corresponding to a sequence of the present invention can be obtained by direct injection of the polypeptide into an animal or by administering the polypeptide to an animal such as a mouse, rabbit, goat or human. A mouse, rabbit or goat is preferred. The antibody so obtained then will bind the polypeptide itself. In this manner, even a sequence encoding only a fragment of the polypeptide can be used to generate antibodies that bind the native polypeptide. Such antibodies can then be used to isolate the polypeptide from test samples such as tissue suspected of containing that polypeptide. For preparation of monoclonal antibodies, any technique which provides antibodies produced by continuous cell line cultures can be used. Examples include the hybridoma technique as described by Kohler and Milstein, *Nature* 256: 495–497 (1975), the trioma technique, the human B-cell hybridoma technique as described by Kozbor et al, *Immun. Today* 4: 72 (1983), and the EBV-hybridoma technique to produce human monoclonal antibodies as described by Cole, et al., in *Monoclonal Antibodies and Cancer Therapy*, Alan R. Liss, Inc, New York, N.Y., pp. 77–96 (1985). Techniques described for the production of single chain antibodies can be adapted to produce single chain antibodies to immunogenic polypeptide products of this invention. See, for example, U.S. Pat. No. 4,946,778, which is incorporated herein by reference.

Various assay formats may utilize the antibodies of the present invention, including "sandwich" immunoassays and probe assays. For example, the monoclonal antibodies or fragment thereof of the present invention can be employed in various assay systems to determine the presence, if any, of prostate tumor derived polypeptide in a test sample. For example, in a first assay format, a polyclonal or monoclonal antibody or fragment thereof, or a combination of these antibodies, which has been coated on a solid phase, is contacted with a test sample, to form a first mixture. This first mixture is incubated for a time and under conditions sufficient to form antigen/antibody complexes. Then, an indicator reagent comprising a monoclonal or a polyclonal antibody or a fragment thereof, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of a prostate tumor derived polypeptide antigen present in the test sample and captured on the solid phase, if any, is determined by detecting the measurable signal generated by the signal generating compound. The amount of prostate tumor derived polypeptide antigen present in the test sample is proportional to the signal generated.

Or, a polyclonal or monoclonal prostate tumor-derived polypeptide antibody or fragment thereof, or a combination of these antibodies which is bound to a solid support, the test sample and an indicator reagent comprising a monoclonal or polyclonal antibody or fragments thereof, which specifically binds to prostate tumor derived polypeptide antigen, or a combination of these antibodies to which a signal generating compound is attached, are contacted to form a mixture. This mixture is incubated for a time and under conditions sufficient to form antibody/antigen/antibody complexes. The presence, if any, of prostate tumor derived polypeptide present in the test sample and captured on the solid phase is determined by detecting the measurable signal generated by the signal generating compound. The amount of prostate tumor derived polypeptide proteins present in the test sample is proportional to the signal generated.

In another assay format, one or a combination of at least two monoclonal antibodies of the invention can be employed as a competitive probe for the detection of antibodies to prostate tumor derived polypeptide protein. For example, prostate tumor derived polypeptide proteins such as the recombinant antigens disclosed herein, either alone or in combination, are coated on a solid phase. A test sample suspected of containing antibody to prostate tumor derived polypeptide antigen then is incubated with an indicator reagent comprising a signal generating compound and at least one monoclonal antibody of the invention for a time and under conditions sufficient to form antigen/antibody complexes of either the test sample and indicator reagent bound to the solid phase or the indicator reagent bound to the solid phase. The reduction in binding of the monoclonal antibody to the solid phase can be quantitatively measured.

In yet another detection method, each of the monoclonal or polyclonal antibodies of the present invention can be employed in the detection of prostate tumor derived polypeptide antigens in fixed tissue sections, as well as fixed cells by immunohistochemical analysis. Cytochemical analysiantibodiesthese antibodies are labeled directly (with, for example, fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

In addition, these monoclonal antibodies can be bound to matrices similar to CNBr-activated Sepharose and used for the affinity purification of specific prostate tumor derived polypeptide proteins from cell cultures or biological tissues such as to purify recombinant and native prostate tumor derived polypeptide antigens and proteins.

The monoclonal antibodies of the invention can also be used for the generation of chimeric antibodies for therapeutic use, or other similar applications.

The monoclonal antibodies or fragments thereof can be provided individually to detect prostate tumor derived polypeptide antigens. Combinations of the monoclonal antibodies (and fragments thereof) provided herein also may be used together as components in a mixture or "cocktail" of at least one prostate tumor derived polypeptide antibody of the invention with antibodies to other prostate tumor derived polypeptide regions, each having different binding specificities. Thus, this cocktail can include the monoclonal antibodies of the invention which are directed to prostate tumor derived polypeptide proteins of prostate tumors and other monoclonal antibodies to other antigenic determinants of prostate tumor derived polypeptide genome.

The polyclonal antibody or fragment thereof which can be used in the assay formats should specifically bind to a prostate tumor derived polypeptide region or other prostate tumor derived polypeptide proteins used in the assay. The polyclonal antibody used preferably is of mammalian origin; human, goat, rabbit or sheep anti-prostate tumor derived polypeptide polyclonal antibody can be used. Most preferably, the polyclonal antibody is rabbit polyclonal anti-prostate tumor derived polypeptide antibody. The polyclonal antibodies used in the assays can be used either alone or as a cocktail of polyclonal antibodies. Since the cocktails used in the assay formats are comprised of either monoclonal antibodies or polyclonal antibodies having different prostate tumor derived polypeptide specificity, they would be useful for diagnosis, evaluation and prognosis of prostate tumor derived polypeptide condition, as well as for studying prostate tumor derived polypeptide protein differentiation and specificity.

It is contemplated and within the scope of the present invention that the prostate tumor derived polypeptide may be detectable in assays by use of a recombinant antigen as well as by use of a synthetic peptide or purified peptide, which contains an amino acid sequence of prostate tumor derived polypeptide. It also is within the scope of the present invention that different synthetic, recombinant or purified peptides identifying different epitopes of the prostate tumor derived polypeptide can be used in combination in an assay to diagnose, evaluate, or prognose the prostate tumor disease condition. In this case, these peptides can be coated onto one solid phase, or each separate peptide may be coated on separate solid phases, such as microparticles, and then combined to form a mixture of peptides which can be later used in assays. Furthermore, it is contemplated that multiple peptides which define epitopes from different polypeptides may be used in combination to make a diagnosis, evaluation, or prognosis of prostate tumor disease. Peptides coated on solid phases or labelled with detectable lables are then allowed to compete with peptides from a patient sample for a limited amount of antibody. A reduction in binding of the synthetic, recombinant, or purified peptides to the antibody (or antibodies) is an indication of the presence of prostate tumor-secreted polypeptides in the patient sample which in turn indicates the presence of prostate tumor, especially prostate cancer, in the patient. Such variations of assay formats are known to those of ordinary skill in the art and are discussed herein below.

In another assay format, the presence of antibody and/or antigen to prostate tumor derived polypeptide can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, recombinant antigens derived from human expression systems may be utilized as well as monoclonal antibodies produced from the proteins derived from the mammalian expression systems as disclosed herein. Such assay systems are described in greater detail in EP Publication No. 0473065.

In yet other assay formats, the polypeptides disclosed herein may be utilized to detect the presence of anti-prostate tumor derived polypeptide in test samples. For example, a test sample is incubated with a solid phase to which at least one recombinant protein has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of prostate tumor derived polypeptide antibody. Other assay formats utilizing the recombinant antigens disclosed herein are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from a second source different from the first source. For example, a recombinant protein derived from a first source such as *E. coli* is used as a capture antigen on a solid phase, a test sample is added to the so-prepared solid phase, and a recombinant protein derived from a different source (i.e., non-*E. coli*) is utilized as a part of an indicator reagent. Likewise, combinations of a recombinant antigen on a solid phase and synthetic peptide in the indicator phase also are possible. Any assay format which utilizes an antigen specific for prostate tumor derived polypeptide from a first source as the capture antigen and an antigen specific for prostate tumor derived polypeptide from a different second source are contemplated. Thus, various combinations of recombinant antigens, as well as the use of synthetic peptides, purified proteins, and the like, are within the scope of this invention. Assays such as this and others are described in U.S. Pat. No. 5,254,458, which enjoys common ownership and is incorporated herein by reference.

Other embodiments which utilize various other solid phases also are contemplated and are within the scope of this invention. For example, ion capture procedures for immobilizing an immobilizable reaction complex with a negatively charged polymer (described in EP publication 0326100 and EP publication No. 0406473), can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in EPO Publication No. 0 273,115.

Also, the methods of the present invention can be adapted for use in systems which utilize microparticle technology including in automated and semi-automated systems wherein the solid phase comprises a microparticle (magnetic or non-magnetic). Such systems include those described in published EPO applications Nos. EP 0 425 633 and EP 0 424 634, respectively.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

It is contemplated that the reagent employed for the assay can be provided in the form of a test kit with one or more containers such as vials or bottles, with each container containing a separate reagent such as a probe, primer, monoclonal antibody or a cocktail of monoclonal antibodies, or a polypeptide (either recombinant or synthetic) employed in the assay. Other components such as buffers, controls, and the like, known to those of ordinary skill in art, may be included in such test kits. It also is contemplated to provide test kits which have means for collecting test samples comprising accessible body fluids, eg. blood, urine, saliva, and stool. Such collection means include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. The collection materials also may be treated with or contain preservatives, stabilizers or antimicrobial agents to help maintain the integrity of the specimens. Test kits designed for the collection, stabilization, and preservation of test specimens obtained by surgery or needle biopsy are also useful. It is contemplated that all kits may be configured in two components; one component for collection and transport of the specimen, and the other component for the analysis of the specimen. Further, kits for the collection, stabilization, and preservation of test specimens may be configured for use by untrained personnel and may be available in the open market for use at home with subsequent transportation to a laboratory for analysis of the test sample.

*E. coli* bacteria (clone 1512846) has been deposited at the American Type Culture Collection (A.T.C.C.), 12301 Parklawn Drive, Rockville, Md. 20852, as of Nov. 7, 1996, under the terms of the Budapest Treaty and will be maintained for a period of thirty (30) years from the date of deposit, or for five (5) years after the last request for the deposit, or for the enforceable period of the U.S. patent, whichever is longer. The deposit and any other deposited material described herein are provided for convenience only, and are not required to practice the present invention in view of the teachings provided herein. The cDNA sequence in all of the deposited material is incorporated herein by reference. Clone 1512846 was accorded A.T.C.C. Deposit No 98243.

The present invention will now be described by way of examples, which are meant to illustrate, but not to limit, the scope of the present invention.

EXAMPLES

Example 1

Identification of Prostate Tumor Library EST Clones

A. Library Comparison of Expressed Sequence Tags (ESTs) or Transcript Images

Partial sequences of cDNA clone inserts, so-called expressed sequence tags (ESTs), were derived from cDNA libraries made from prostate tumor tissues, prostate non-tumor tissues, and numerous other tissues, both diseased and normal, and entered into a database (LIFESEQ™ database, available from Incyte Pharmaceuticals, Palo Alto, Calif.) as gene transcript images. See J. Seilhamer, et al., WO 95/20681. A transcript image is a listing giving the abundance of ESTs in a given tissue and represents the activity of genes in the tissue. The transcript images then were evaluated to identify EST sequences that were representative primarily of the tumor libraries. These target clones then were ranked according to their abundance (occurrence) in the target libraries and absence from background libraries. Higher abundance clones with low background occurrence were given higher study priority. The sequence of the present invention was found to be upregulated in prostate tumor tissue when compared to prostate non-tumor tissue or to non-prostate tissue. The consensus sequence was found in seven of nine prostate tumor libraries (77.8%). Nineteen occurrences were found out of a total population of 34,497 prostate tumor sequences (0.055%). The consensus sequence was found in three of 11 prostate non-tumor libraries (27.3%). Three occurrences were found out of a total population of 42,702 prostate non-tumor sequences (0.0070%). The consensus sequence was found in 15 of 241 non-prostate libraries (6.2%). Eighteen occurrences were found out of a total population of 1,071,076 non-prostate sequences (0.0017%). The consensus sequence thus exhibits pronounced upregulation and overexpression in prostate tumors, with respect to both occurrence in libraries and occurrence as a percent of total sequences present. SEQUENCE ID NOS 1–8, corresponding to clones g885075, 1512846, 1699634, 1444924, 1209763, 612079, 608177 and 842007, respectively, were identified for further study. These sequences represent the minimum amount of sequences which were required to unambiguously define the full consensus sequence.

B. Generation of a Consensus Sequence

SEQUENCE ID NOS 1–8 were placed in the Sequencher™ Program (available from Gene Codes Corporation, Ann Arbor, Mich., in order to generate a nucleotide alignment of clones g885075 (SEQUENCE ID NO 1), 1512846 (SEQUENCE ID NO 2), 1699634 (SEQUENCE ID NO 3), 1444924 (SEQUENCE ID NO 4), 1209763 (SEQUENCE ID NO 5), 612079 (SEQUENCE ID NO 6), 608177 (SEQUENCE ID NO 7), and 842007 (SEQUENCE ID NO 8), along with their consensus sequence (SEQUENCE ID NO 9). FIG. 1A 1–3 shows the nucleotide alignment of these clones and FIG. 1B presents the consensus nucleotide sequence (SEQUENCE ID NO 9) of these clones. Then, a three frame translation was performed on the consensus sequence (SEQUENCE ID NO 9). The first forward frame is presented as SEQUENCE ID NOS 10–18, the second forward frame is presented as SEQUENCE ID NOS 19–30, and the third forward frame is presented as SEQUENCE ID NOS 31–36.

Example 2

Sequencing of EST-Containing Clones

DNA sequences for clones which comprise the most upstream and downstream ESTs of the contig are determined using dideoxy termination sequencing with either dye terminators or radiolabeled nucleotides, following known methods. See, for example, F. Sanger et al., *Proc. Natl. Acad. Sci. U.S.A.*, 74: 5463.

Because the vector pSPORT1 (Life Technologies, Gaithersburg, Md.) contains universal priming sites just adjacent to the 3' and 5' ligation junctions of the inserts, the inserts are sequenced in both directions using universal primers. The sequencing reactions are run on a polyacrylamide denaturing gel and the sequences are determined by an Applied Biosystems 377 Sequencer (available from Applied Biosystems, Foster City, Calif.) or other sequencing apparatus.

Example 3

Nucleic Acid Preparation

A. RNA Extraction from Tissue

Total RNA is isolated from solid tissues or cells from patients with prostate cancer and non-tumor tissues using a lithium chloride/urea technique known in the art and described by N. Kato et al., *J. Virology* 61: 2182–2191 (1987). Non-tumor tissues are used as negative controls. The mRNA can be further purified from total RNA using commercially available kits such as oligo dT cellulose spin columns (RediCol™ from Pharmacia, Uppsala, Sweden) for the isolation of poly-adenylated RNA. Total or mRNA then is dissolved in lysis buffer (5M guanidine thiocyanate, 0.1M EDTA, pH 7.0) for analysis in the ribonuclease protection assay.

B. RNA Extraction from Blood

RNA is prepared from blood samples from patients with or without diagnosed prostate cancer by the standard QIAamp (Qiagen, Chattsworth, Calif.) RNA protocol. Briefly, 25 $\mu$l of blood are mixed with 280 $\mu$l of Qiagen AVL buffer and incubated at room temperature for 15 min. Then, 280 $\mu$l of 100% ethanol is added to the mixture and the entire mixture is transferred to a QIAamp spin column. Next, the column is spun at 6,000×g for 2 min, washed twice with 500 $\mu$l of Qiagen AW/ethanol buffer and spun at 6,000×g for 2 min. The column is spun an additional 3 min at >10,000×g. The RNA is eluted by adding 100 $\mu$l of RNase-free water preheated at 80° C. to the column and spinning at 6,000×g for 2 min.

C. RNA Extraction from polysomes

Tissue is minced in saline at 4° C. and mixed with 2.5 volumes of 0.8M sucrose in a $TK_{150}M$ (150 mM KCl, 5 mM $MgCl_2$, 50 mM Tris-HCl, pH 7.4) solution containing 6 mM 2-mercaptoethanol. The tissue is homogenized in a Teflon-glass Potter homogenizer with five strokes at 100–200 rpm followed by six strokes in a Dounce homogenizer, as described by B. Mechler, *Methods in Enzymology* 152: 241–248 (1987). The homogenate then is centrifuged at 12,000×g for 15 min at 4° C. to sediment the nuclei. The polysomes are isolated by mixing 2 ml of the supernatant with 6 ml of 2.5M sucrose in $TK_{150}M$ and layering this mixture over 4 ml of 2.5M sucrose in $TK_{150}M$ in a 38 ml polyallomer tube. Two additional sucrose $TK_{150}M$ solutions are successively layered onto the extract fraction; a first layer of 13 ml 2.05M sucrose followed by a second layer of 6 ml of 1.3M sucrose. The polysomes are isolated by centrifuging the gradient at 90,000×g for 5 h at 4° C. The fraction then is taken from the 1.3M sucrose/2.05M sucrose interface with a siliconized pasteur pipette and diluted in an equal volume of TE (10 mM Tris-HCl, pH 7.4, 1 mM EDTA). An equal volume of 90° C. SDS buffer (1% SDS, 200 mM NaCl, 20 mM Tris-HCl, pH 7.4 is added and the solution is incubated in a boiling water bath for 2 min. Proteins next are digested with a proteinase-K digestion (50 mg/ml) for 15 min at 37° C. The mRNA is purified with 3 equal volumes of phenol-chloroform extractions followed by precipitation with 0.1 volume of 2M sodium acetate (pH 5.2) and 2 volumes of 100% ethanol at −20° C. overnight. The precipitated RNA is recovered by centrifugation at 12,000×g for 10 min at 4° C. The RNA is dried and resuspended in TE, pH 7.4 or distilled water. The resuspended RNA then can be used in a slot blot or dot blot hybridization assay to check for the presence of mRNA containing EST sequences (see example 6).

The quality of nucleic acid and proteins is dependent on the method of preparation used. Each sample may require a different preparation technique to maximize isolation efficiency of the target molecule.

Example 4

Ribonuclease Protection Assay

A. Labeling of Complementary RNA (cRNA) Hybridization Probes

Labeled sense and antisense riboprobes are transcribed from the EST sequence which contains a 5' RNA polymerase promoter such as SP6 or T7. The sequence may be from a vector containing the appropriate EST insert or from a PCR-generated product of the insert using PCR primers which incorporate a 5' RNA polymerase promoter sequence. The transcripts are prepared in a 20 µl reaction volume containing 1 µg of DNA template, 2 µl of 100 mM dithiothreitol, 0.8 µl of RNasin (10–40 U), 500 µM each of ATP, CTP, GTP, 5 µl (alpha $^{32}$P) UTP or 100–500 µM biotinylated UTP, and 1 µl of RNA polymerase in transcription buffer (40 mM Tris-HCl, pH 7.5, 6 mM $MgCl_2$, 2 mM spermidine HCl, 5 mM NaCl). Following incubation at 37° C. for one hour, the transcripts are treated with DNase I (15 U) for an additional 30 min to digest the template. The probes then are isolated by spin columns, salt precipitation or electrophoresis techniques which are well-known in the art. Finally, the probes are dissolved in lysis buffer (5M Guanidine Thiocyanate, 0.1M EDTA, pH 7.0).

B. Hybridization of Labeled Probe to Target

Approximately 20 µg of extracted total cellular RNA, as obtained in Example 3 supra, in 10 µl of lysis buffer are mixed with either (i) 1×10$^5$ cpm of radioactively labeled probe or (ii) 250 pg of non-isotopically labeled probe, each in 2 µl of lysis buffer. The mixture then is incubated at 60° C. for 5 min and hybridized overnight at room temperature. See, T. Kaabache et al., *Anal. Biochem.* 232: 225–230 (1995).

C. RNase Digestion

Hybridizations are terminated by incubation with 380 µl of a solution containing 40 βg/ml RNase A and 625 units/ml RNase T1 in 1 mM EDTA, 300 mM NaCl, 30 mM Tris-HCl pH 7.4 for 45–60 min at room temperature. RNase digestion then is terminated by the addition of 60 µl of proteinase-K (1.7 mg/ml) containing 3.3% SDS, followed by incubation for 30 min at 37° C. The digested mixture then is extracted with phenol:chloroform:isoamyl alcohol to remove protein. The mRNA:cRNA hybrids are precipitated from the aqueous phase by the addition 4 µg yeast tRNA and 800 µl of ethanol, and incubation at −80° C. for 30 min. The precipitates are collected by centrifugation.

D. Fragment Analysis

The precipitates are dissolved in 5 µl of denaturing gel loading dye (80% formamide, 10 mM EDTA, pH 8.0, 1 mg/ml xylene cyanol, 1 mg/ml bromophenol blue) and electrophoresed in 6% polyacrylamide TBE, 8M urea denaturing gels. The gels are dried under vacuum and autoradiographed. Quantitation can be performed by comparing the counts obtained from the test samples to a calibration curve that was generating by utilizing calibrators that are the sense strand. In cases where non-isotopic labels are used, hybrids are transferred from the gels to membranes (nylon or nitrocellulose) by blotting and then analyzed using detection systems that employ streptavidin alkaline phosphatase conjugates and chemiluminesence or chemifluoresence reagents. High level of expression of mRNA corresponding to SEQUENCE ID NOS 1–9 then is an indication of the presence of prostate tumor.

Example 5

Northern Blotting

The northern blot technique is used to identify a specific size RNA fragment from a complex population of RNA using gel electrophoresis and nucleic acid hybridization. Northern blotting is well-known technique in the art. Briefly, up to 20 µg of extracted RNA (see Example 3) are incubated in 20 µl of a solution containing 40 mM morphilinopropanesulfonic acid (MOPS), pH 7.0, 10 mM sodium acetate, 1 mM EDTA, 2.2M formaldehyde, 50% v/v formamide for 15 min at 55° C. The denatured RNA is mixed with 2 µl of loading buffer (50% glycerol, 1 mM EDTA, 0.4% bromophenol blue, 0.4% xylene cyanol) and loaded into a denaturing 1.5% agarose gel containing 40 mM morphilinopropanesulfonic acid (MOPS), pH 7.0, 10 mM sodium acetate, 1 mM EDTA and 2.2M formaldehyde. The gel is electrophoresed for an appropriate time, transferred to a wash tray and washed with five changes of RNase free water for 5 min followed by a 45 min soak at room temperature in 50 mM NaOH and 10 mM NaCl. The gel is neutralized by soaking for 45 min in 0.1M Tris-HCl, pH 7.5. After a 1 h soak in 20× SSC buffer (3M NaCl, 300 mM tri-sodium citrate), the gel is transferred onto a nitrocellulose or nylon based matrix. After transfer is complete, the filter is washed in 3× SSC, air dried for 2 h and baked at 80° C. for 4 h under vacuum. The mRNAs are detected as in example 4, supra. Again, high level of expression of mRNA corresponding to SEQUENCE ID NOS 1–9 is an indication of the presence of prostate tumor.

Example 6

Dot Blot/Slot Blot

Dot and slot blot assays are quick methods to evaluate the presence of a specific nucleic acid sequence in a complex mix of nucleic acid.

To perform, up to 20 µg of RNA is mixed in 50 µl of 50% formamide, 7% formaldehyde, 1× SSC, incubate 15 min at 68° C. and cool on ice. Then, 100 µl of 20× SSC is added to the RNA mixture and loaded under vacuum onto a manifold apparatus that has a prepared nitrocellulose or nylon membrane. The membrane is soaked in water, 20× SSC for 1 hour, placed on two sheets of 20× SSC prewet Whatman #3 filter paper, and loaded into a slot blot or dot blot vacuum manifold apparatus. The slot blot is analyzed with probes prepared and labeled as in the example 4 supra. Detection of mRNA corresponding SEQUENCE ID NOS 1–9 is an indication of the presence of prostate tumor.

Other methods and buffers not specifically detailed for examples 5 and 6 are described in J. Sambrook et al, supra.

Example 7

In Situ Hybridization

This method is useful to directly detect specific target nucleic acid sequences in cells using detectable nucleic acid hybridization probes.

Tissues are prepared with cross-linking fixatives agents such as paraformaldehyde or glutaraldehyde for maximum cellular RNA retention. See, L. Angerer et al., *Methods in Cell Biol.* 35: 37–71 (1991). Briefly, the tissue is placed in greater than 5 volumes of 1% glutaraldehyde in 50 mM sodium phosphate, pH 7.5 at 4° C. for 30 min. The solution is changed with fresh solution for a further 30 min fixing. The fixing solution should have an osmolality of approximately 0.375% NaCl. The tissue is washed once in isotonic NaCl to remove the phosphate.

The fixed tissues then are embedded in paraffin, as follows. The tissue is dehydrated though a series of ethanol concentrations for 15 min each: 50% twice, 70% twice, 85%, 90% and 100% twice. The tissue next is soaked in two changes of xylene for 20 min each at room temperature; then it is soaked in two changes of 1 xylene: 1 paraffin for 20 min each at 60° C.; and then it is soaked in three final changes in paraffin for 15 min each.

The tissue next is cut in 5 $\mu$m sections using a standard microtome and placed on a slide previously treated with the tissue adhesive 3-aminopropyltriethoxysilane.

Paraffin is removed from the tissue by two 10 min xylene soaks and rehydrated in a series of ethanol concentrations; 99% twice, 95%, 85%, 70%, 50%, 30% and distilled water twice. The sections are pre-treated with 0.2M HCl for 10 min and permeabilized with 2 $\mu$g/ml Proteinase-K at 37° C. for 15 min.

Labeled riboprobes transcribed from the EST pSPORT1 plasmid (see example 4) are hybridized to the prepared tissue sections and hybridized overnight at 56° C. in 3× standard saline extract and 50% formamide. Excess probe is removed by washing in 2× standard saline citrate and 50% formamide followed by digestion with 100 $\mu$g/ml RNase A at 37° C. for 30 min. Fluorescence probe is visualized by illumination with UV light under a microscope. Fluorescence in the cytoplasm is indicative of mRNA production. Fluorescence in the nucleus detects the presence of genomic material. Alternatively, the sections can be visualized by autoradiography.

Example 8

Reverse Transcription PCR

A. One Step RT-PCR Assay

Target-specific primers are designed to detect the above target sequence by reverse transcription PCR by methods known in the art. One step RT-PCR is a sequential procedure that performs both RT and PCR in a single reaction mixture. The procedure is performed in a 200 $\mu$l reaction mixture containing 50 mM (N,N,-bis[2-Hydroxyethyl]glycine), pM 8.15, 81.7 mM KOAc, 33.33 mM KOH, 0.01 mg/ml bovine serum albumin, 0.1 mM ethylene diaminetetraacetic acid, 0.02 mg/ml NaN$_3$, 8% w/v glycerol, 150 $\mu$M each of dNTP, 0.25 $\mu$M each primer, 5 U rTth polymerase, 3.25 mM Mn(OAc)$_2$, and 5 $\mu$l blood equivalents of target (see example 3). Since RNA and the rTth polymerase enzyme are unstable in the presence of Mn(OAc)$_2$, the Mn(OAc)$_2$ should be added just before target addition. Optimal conditions for cDNA synthesis and thermal cycling readily can be determined by those skilled in the art. The reaction is incubated in a Perkin-Elmer Thermal Cycler 480. Optimal conditions for cDNA synthesis and thermal cycling can readily be determined by those skilled in the art. Conditions which may be found useful include cDNA synthesis at 60°–70° for 15–45 min, and 30–45 amplification cycles at 94° C., 1 min; 55° C.–70° C., 1 min; 72° C., 2 min. One step RT-PCR also may be performed by using a dual enzyme procedure with Taq polymerase and a reverse transcriptase enzyme, such as MMLV or AMV RT enzymes.

B. Traditional RT-PCR

Alternatively, a traditional two step RT-PCR reaction may be performed, as described by K. -Q. Hu et al., *Virology* 181: 721–726 (1991), as follows: The extracted mRNA is transcribed in a 25 $\mu$l reaction mixture containing 10 mM Tris-HCl, pH 8.3, 5 mM MgCl$_2$, 500 $\mu$M dNTP, 20 U RNasin, 1 $\mu$M antisense primer, and 25 U AMV (avian myeloblastosis virus) or MMLV (Moloney murine leukemia virus) reverse transcriptase. Reverse transcription is performed at 37–45° C. for 30–60 min, followed by further incubation at 95° C. for 5 min to inactivate the RT. PCR is performed using 10 $\mu$l of the cDNA reaction in a final PCR reaction volume of 50 $\mu$l containing 10 mM Tris-HCl, pH 8.3, 50 mM KCl, 2 mM MgCl$_2$, 200 $\mu$M dNTP, 0.5 $\mu$M of each primer and 2.5 U of Taq polymerase. Optimal conditions for cDNA synthesis and thermal cycling can be readily determined by those skilled in the art. The reaction is incubated in a Perkin-Elmer Thermal Cycler 480. Conditions which may be found useful include 30–45 cycles of amplification (94° C., 1 min; 55°–70° C., 1 min; 72° C., 2 min), final extension (72° C., 10 min) and soak at 4° C.

C. PCR Fragment Analysis

The correct products can then be verified by size determination using gel electrophoresis with fluorescent intercalators or by southern blotting techniques using a labeled probes against the internal sequences of the PCR product. The probes may also be polynucleotides analogs, such as morpholinos or peptide nucleic acids (PNA). Detection of SEQUENCE ID NOS. 1–9 or any fragment thereof is then indicative of the presence of prostate tumor, especially prostate cancer.

Example 9

OH-PCR

A. Probe selection and Labeling

Target-specific primers and probes are designed to detect the above target sequence by oligonucleotide hybridization PCR. Publications WO 92/10505, published Jun. 25, 1992 and WO 92/11388 published Jul. 9, 1992 teach methods for labeling oligonucleotides at their 5' and 3' ends, respectively. According to one known method for labeling an oligonucleotide, a label-phosphoramidite reagent is prepared and used to add the label to the oligonucleotide during its synthesis. For example, see N. T. Thuong et al., *Tet. Letters* 29(46): 5905–5908 (1988); or J. S. Cohen et al., published U.S. patent application Ser. No. 07/246,688 (NTIS ORDER No. PAT-APPL-7-246,688) (1989). Preferably, probes are labeled at their 3' end to prevent participation in PCR and the formation of undesired extension products. For one step OH-PCR the probe should have a $T_M$ at least 15° C. below the $T_M$ of the primers. The primers and probes are labeled with either capturable or detectable moieties using standard phosphoramidite chemistry which is well-known to one skilled in the art.

B. One Step Oligo Hybridization PCR

OH-PCR is performed on a 200 $\mu$l reaction containing 50 mM (N,N,-bis[2-Hydroxyethyl]glycine), pH 8.15, 81.7 mM KOAc, 33.33 mM KOH, 0.01 mg/ml bovine serum albumin, 0.1 mM ethylene diaminetetraacetic acid, 0.02 mg/ml NaN$_3$, 8% w/v glycerol, 150 $\mu$M each of dNTP, 0.25 $\mu$M each primer, 3.75 nM probe, 5 U rTth polymerase, 3.25 mM Mn(OAc)$_2$, and 5 $\mu$l blood equivalents of target (see example 3). Since RNA and the rTth polymerase enzyme are unstable in the presence of Mn(OAc)$_2$, the Mn(OAc)$_2$ should be added just before target addition. The reaction is incubated in a Perkin-Elmer Thermal Cycler 480. Optimal conditions for cDNA synthesis and thermal cycling can be readily determined by those skilled in the art. Conditions which may be found useful include cDNA synthesis (60° C., 30 min), 30–45 amplification cycles (94° C., 40 sec; 55–70° C., 60 sec), oligo-hybridization (97° C., 5 min; 15° C., 5 min; 15° C. soak). The correct reaction product contains at least one of the strands of the PCR product and an internally hybridized probe.

C. OH-PCR product analysis

Amplified reaction products are detected on an LCx® analyzer system (available from Abbott Laboratories, Abbott Park, Ill. Briefly, the correct reaction product is captured by an antibody labeled microparticle at a capturable site on either the PCR product strand or the hybridization probe, and the complex is detected by binding of a detectable antibody conjugate to either a detectable site on the probe or the PCR strand. Only a complex containing a PCR strand hybridized with the internal probe is detectable. The detection of this complex is then indicative of the presence of a prostate tumor.

Many other detection formats exist which can be used to detect the presence of the EST containing nucleic acid sequence. The sequence may also be detected by other methods including but not limited to, ligase chain reaction (LCR, Abbott Laboratories, Abbott Park, Ill.); Q-beta replicase (Gene-Trak™, Naperville, Ill.), branched chain reaction (Chiron, Emeryville, Calif.), and strand displacement assays (Becton Dickinson, Research Triangle Park, N.C.).

Example 10

Synthetic Peptide Production

Synthetic peptides (SEQUENCE ID NOS 10–36 or fragments thereof) are prepared based upon the predicted amino acid sequence of the EST polypeptide (see example 1). All peptides are synthesized on an ABI Peptide Synthesizer (available from Applied Biosciences, LOCATION), Model 431A, using FMOC chemistry, standard cycles and DCC-HOBt activation. Cleavage and deprotection conditions are as follows: the resin is added to 20 ml trifluoroacetic acid (TFA), 0.3 ml water, 0.2 ml ethanedithiol, 0.2 ml thioanisole and 100 mg phenol, and stirred at room temperature for 1.5 hours. The resin then is filtered by suction and the peptide is obtained by precipitation of the TFA solution with ether followed by filtration. Each peptide is purified via reverse-phase preparative HPLC using a water/acetonitrile/0.1% TFA gradient and lyophilized. The product is confirmed by mass spectrometry (see example 12).

Disulfide bond formation is accomplished using auto-oxidation conditions, as follows: the peptide is dissolved in a minimum amount of DMSO (approximately 10 ml) before adding buffer (0.1M Tris-HCl, pH 6.2) to a concentration of 0.3–0.8 mg/ml. The reaction is monitored by HPLC until complete formation of the disulfide bond, followed by reverse-phase preparative HPLC using a water/acetonitrile/0.1% TFA gradient and lyophilization. The product then is confirmed by mass spectrometry (see example 12).

The purified peptides can be conjugated to Keyhole Limpet Hemocyanin or other immunoreactive molecule with glutaraldehyde, mixed with adjuvant, and injected into animals.

Example 11

Expression of Protein in a Cell Line

A. Construction of EST Expression Plasmid

Plasmid 577, described in U.S. patent application Ser. No. 08/478,073, filed Jun. 7, 1995 and incorporated herein by reference, has been constructed for the expression of secreted antigens in a permanent cell line. This plasmid contains the following DNA segments: (a) a 2.3 Kb fragment of pBR322 containing bacterial betalactamase and origin of DNA replication; (b) a 1.8 Kb cassette directing expression of a neomycin resistance gene under control of HSV-1 thymidine kinase promoter and poly-A addition signals; (c) a 1.9 Kb cassette directing expression of a dihydrofolate reductase gene under the control of an SV-40 promoter and poly-A addition signals; (d) a 3.5 Kb cassette directing expression of a rabbit immunoglobulin heavy chain signal sequence fused to a modified hepatitis C virus (HCV) E2 protein under the control of the Simian Virus 40 T-Ag promoter and transcription enhancer, the hepatitis B virus surface antigen (HBsAg) enhancer I followed by a fragment of Herpes Simplex Virus-1 (HSV-1) genome providing poly-A addition signals; and (e) a residual 0.7 Kb fragment of Simian Virus 40 genome late region of no function in this plasmid. All of the segments of the vector were assembled by standard methods known to those skilled in the art of molecular biology.

Plasmids for the expression of secretable EST proteins are constructed by replacing the hepatitis C virus E2 protein coding sequence in plasmid 577 with those from the EST sequence selected from SEQUENCE ID NOS 10–36 or fragments thereof, as follows. Digestion of plasmid 577 with Xbal releases the hepatitis C virus E2 gene fragment. The resulting plasmid backbone allows insertion of the EST insert downstream of the rabbit immunoglobulin heavy chain signal sequence which directs the expressed proteins into the secretory pathway of the cell. The EST fragment is generated by PCR using standard procedures. Encoded in the sense PCR primer sequence is an Xba 1 site, immediately followed by a 12 nucleotide sequence that encodes the amino acid sequence Ser-Asn-Glu-Leu ("SNEL") to promote signal protease processing, efficient secretion and final product stability in culture fluids. Immediately following this 12 nucleotide sequence the primer contains nucleotides complementary to template sequences encoding amino acids of the EST sequence. The antisense primer incorporates a sequence encoding the eight amino acids Asp-Tyr-Lys-Asp-Asp-Asp-Asp-Lys just before the stop codons. Within this sequence is the recognition site for a monoclonal antibody (MAb) designated anti-FLAG M2 (Eastman Kodak, Co., New Haven, Conn.). It is incorporated to aid in analysis and purification of the EST protein product. PCR is performed using GeneAmp® reagents obtained from Perkin-Elmer-Cetus, essentially as directed by the supplier's instructions. PCR primers are used at a final concentration of 0.5 $\mu$M. PCR is performed on the pSPORT1 plasmid template in a 100 $\mu$l reaction for 35 cycles (94° C., 30 seconds; 55° C., 30 seconds; 72° C., 90 seconds) followed by an extension cycle of 72° C. for 10 min.

B. Transfection of Dihydrofolate Reductase Deficient Chinese Hamster Ovary Cells The plasmid described supra is transfected into CHO/dhfr- cells (DXB-111) (Uriacio, et al., *PNAS* 77, 4451–4466; 1980); these cells are available from the A.T.C.C., 12301 Parklawn Drive, Rockville, Md. 20852, under Accession No. CRL 9096), using the cationic liposome-mediated procedure (P. L. Feigner et al., *PNAS* 84: 7413–7417 [1987]), as follows. CHO/dhfr-cells are cultured in Ham's F-12 media supplemented with 10% fetal calf serum, L-glutamine (1 mM) and freshly seeded into a 25 $cm^2$ flask at a density of 5–8×$10^5$ cells per flask. The cells are grown to between 60 and 80% confluency for transfection. Twenty micrograms of plasmid DNA are added to 1.5 ml of Opti-MEM I medium and 100 μl of Lipofectin Reagent (Gibco-BRL; Grand Island, N.Y.) are added to a second 1.5 ml portion of Opti-MEM I media. The two solutions are mixed and incubated at room temperature for 20 min. The culture medium is removed from cells and the cells are rinsed 3 times with 5 ml of Opti-MEM I medium. The Opti-MEM I-Lipofection-plasmid DNA solution is then overlaid onto the cells. The cells are incubated for 3 h at 37° C., after which time the Opti-MEM I-Lipofectin-DNA solution is replaced with culture medium for an additional 24 h prior to selection.

C. Selection and Amplification

One day after transfection, cells are passaged 1:3 and incubated with dhfr/G418 selection medium (hereafter, "F-12 minus medium G"). Selection medium is Ham's F-12 with L-glutamine and without hypoxanthine, thymidine, and glycine (JRH Biosciences, Lenexa, Kans.), and 300 μg per ml G418 (Gibco-BRL; Grand Island, N.Y.). Media volume to surface area ratios of 5 ml per 25 $cm^2$ are maintained. After approximately two weeks, DHFR/G418 cells are expanded to allow passage and continuous maintenance in F-12 minus medium G.

Amplification of each of the transfected EST genes is achieved by stepwise selection of $DHFR^+$, $G418^+$ cells with methotrexate (reviewed by R. Schimke, *Cell* 37: 705–713 [1984]). Cells are incubated with F-12 minus medium G containing 150 nM methotrexate (MTX) (Sigma, St. Louis, Mo.) for approximately two weeks until resistant colonies appear. Further gene amplification is achieved by selection of 150 nM adapted cells with 5 μM MTX.

D. Antigen Production

F-12 minus medium G supplemented with 5 μM MTX is overlaid onto just confluent monolayers for 12 to 24 h at 37° C. in 5% $CO_2$. The growth medium is removed and the cells are rinsed 3 times with Dulbecco's phosphate buffered saline (PBS) (with calcium and magnesium) (Gibco-BRL; Grand Island, N.Y.), to remove the remaining media/serum which might be present. Cells then are incubated with VAS custom medium (VAS custom formulation with L-glutamine with HEPES without phenol red, available from JRH Bioscience; Lenexa, Kans., product number 52-08678P), for 1 h at 37° C. in 5% $CO_2$. Cells then are overlaid with VAS for production at 5 ml per T 25 $cm^2$ flask. The medium is removed after 7 days of incubation and then frozen to await purification with harvests 2, 3 and 4. The monolayers are overlaid with VAS for 3 more 7-day harvests.

E. Analysis of Prostate Antigen Expression

Aliquots of VAS supernatants from the cells expressing the EST protein construct are analyzed either by SDS-polyacrylamide gel electrophoresis (SDS-PAGE) using standard methods and reagents known in the art (Laemmli discontinuous gels) or by mass spectrometry.

F. Purification

Purification of the EST protein containing the FLAG sequence is performed by immunoaffinity chromatography using an affinity matrix comprising anti-FLAG M2 monoclonal antibody covalently attached to agarose by hydrazide linkage (Eastman Kodak Co., New Haven, Conn.). Prior to affinity purification, protein in pooled VAS medium harvests from roller bottles is exchanged into 50 mM Tris-HCl pH 7.5, 150 mM NaCl buffer using a Sephadex G-25 (Pharmacia Biotech Inc., Uppsala, Sweden) column. Protein in this buffer is applied to the anti-FLAG M2 antibody affinity column, non-binding protein is eluted by washing the column with 50 mM Tris-HCl pH 7.5, 150 mM NaCl buffer and bound protein is eluted using an excess of FLAG peptide in 50 mM Tris-HCl, pH 7.5, 150 mM NaCl. The excess FLAG peptide can be removed from the EST purified protein by gel electrophoresis.

Then, the largest cloned insert containing the EST region is sub-cloned into either (i) a eukaryotic expression vector which may contain a cytomegalovirus (CMV) promoter and/or protein fusable sequences which aid in protein expression and detection, or (ii) a bacterial expression vector containing a superoxide-dismutase (SOD) and CMP-KDO synthetase (CKS) or other protein fusion gene for expression of the protein sequence. Methods and vectors which are useful for the production of polypeptides which contain fusion sequences of SOD are described in EPO 0196056, published Oct. 1, 1986, and those of CKS are described in EPO Publication No. 0331961, published Sep. 13, 1989. The purified protein can be used in a variety of techniques, including but not limited to animal immunization studies, solid phase immunoassays, etc.

Example 12

Chemical Analysis of Prostate Tumor Proteins

A. Analysis of Tryptic Peptide Fragments Using MS

Serum from a patient with prostate cancer is run on a polyacrylamide gel using standard procedures and stained with Coomassie Blue. Sections of the gel suspected of containing the unknown polypeptide are excised and subjected to an in-gel reduction, acetamidation, and tryptic digestion. P. Jeno et al, *Anal. Bio.* 224: 451–455 (1995), and J. Rosenfeld et al, *Anal. Bio.* 203: 173–179 (1992). The gel sections are washed with 100 mM $NH_4HCO_3$ and acetonitrile. The shrunken gel pieces are swollen in digestion buffer (50 mM $NH_4HCO_3$, 5 mM $CaCl_2$, and 12.5 μg/ml trypsin) at 4° C. for 45 min. The supernatant is aspirated and replaced with 5 to 10 μl of digestion buffer without trypsin and allowed to incubate overnight at 37° C. Peptides are extracted with 3 changes of 5% formic acid and acetonitrile, and evaporated to dryness. The peptides are adsorbed to approximately 0.1 μl of POROS R2 sorbent (Perseptive Biosystems, Framingham, Mass.) trapped in the tip of a drawn gas chromatography capillary tube by dissolving them in 10 μl of 5% formic acid and passing it through the capillary. The adsorbed peptides are washed with water and eluted with 5% formic acid in 60% methanol. The eluant is passed directly into the spraying capillary of an API III mass spectrometer (Perkin-Elmer Sciex, Thornhill, Ontario, Canada) for analysis by nano-electrospray mass spectrometry. M. Wilm et at., *Int. J. Mass Spectrom. Ion Process* 136: 167–180 (1994), and M. Wilm et al., *Anal. Chem.* 66: 1–8 (1994). The masses of the tryptic peptides are determined from the mass spectrum obtained off the first quadrupole. Masses corresponding to predicted peptides can be further analyzed in MS/MS mode to give the amino acid sequence of the peptide.

B. Peptide Fragment Analysis Using LC/MS

The presence of polypeptides predicted from mRNA sequences found in hyperplastic disease tissues also can be confirmed using liquid chromatography/tandem mass spectrometry (LC/MS/MS). D. Hess et al., *METHODS A Companion to Methods in Enzymology* 6: 227–238 (1994). The serum specimen or tumor extract from the patient is denatured with SDS and reduced with dithiothreitol (1.5 mg/ml) for 30 min at 90° C. followed by alkylation with iodoacetamide (4 mg/ml) for 15 min at 25° C. Following acrylamide electrophoresis, the polypeptides are electroblotted to a cationic membrane and stained with Coomassie Blue. Following staining, the membranes are washed and sections thought to contain the unknown polypeptides are cut out and dissected into small pieces. The membranes are placed in 500 μl microcentrifuge tubes and immersed in 10 to 20 μl of proteolytic digestion buffer (100 mM Tris-HCl, pH 8.2, containing 0.1M NaCl, 10% acetonitrile, 2 mM CaCl$_2$, and 5 ug/ml trypsin) (Sigma, St. Louis, Mo.). After 15 h at 37° C., 3 μl of saturated urea and 1 μl of 100 μg/ml trypsin are added, and incubated for an additional 5 h at 37° C. The digestion mixture is acidified with 3 μl of 10% trifluoroacetic acid and centrifuged to separate supernatant from membrane. The supernatant is injected directly onto a microbore, reverse phase HPLC column and eluted with a linear gradient of acetonitrile in 0.05% trifluoroacetic acid. The eluate is fed directly into an electrospray mass spectrometer, after passing though a stream splitter if necessary to adjust the volume of material. The data is analyzed following the procedures set forth in example 12, section A.

Example 13

Gene Immunization Protocol

A. In Vivo Antigen Expression

Gene immunization circumvents protein purification steps by directly expressing an antigen in vivo after inoculation of the appropriate expression vector. Also, production of antigen by this method may allow correct protein folding and glycosylation since the protein is produced in mammalian tissue. The method utilizes insertion of the gene sequence into a plasmid which contains a CMV promoter, expansion and purification of the plasmid, and injection of the plasmid DNA into the muscle tissue of an animal. See, for example, H. Davis et al., *Human Molecular Genetics* 2: 1847–1851 (1993). After one or two booster immunizations, the animal can then be bled, ascites fluid collected or spleen harvested for production of hybridomas.

B. Plasmid Preparation and Purification

EST DNA sequences are generated from the pSPORT1 EST vector using appropriate PCR primers containing suitable 5' restriction sites. The PCR product is cut with appropriate restriction enzymes and inserted into a vector which contains the CMV promoter (for example, pRc/CMV or pcDNA3 vectors from Invitrogen, San Diego, Calif.). This plasmid then is expanded in the appropriate bacterial strain and purified from the cell lysate using a CsCl gradient or a Qiagen plasmid DNA purification column. All these techniques are familiar to one of ordinary skill in the art of molecular biology.

C. Immunization Protocol

Anesthetized animals are immunized intramuscularly with 0.1–100 μg of the purified plasmid diluted in PBS or other DNA uptake enhancers (Cardiotoxin, 25% sucrose). See, for example, H. Davis, et al, *Human Gene Therapy* 4: 733–740 (1993); and P. W. Wolff et al, *Biotechniques* 11: 474–485 (1991). One to two booster injections are given at monthly intervals.

D. Testing and Use of Antiserum

Animals are bled and the sera tested for antibody using peptides synthesized from the known gene sequence (see example 16) such as western blotting or EIA techniques. Antisera produced by this method can then be used to detect the presence of the antigen in a patient's sera or tumor tissue extract by ELISA or Western blotting techniques.

Example 14

Purification of EST peptide specific antibodies from serum

Immune sera is affinity purified using immobilized synthetic peptides by methods known in the art. Antiserum produced against a peptide as described in Example 10 is affinity purified in a variety of ways. An IgG fraction is obtained by passing the diluted, crude antiserum over a Protein A column (Affi-Gel protein A, Bio-Rad, Hercules, Calif.). Elution with Binding Buffer supplied by the manufacturer removes all proteins that are not immunoglobulins. Elution with pH 3 buffered glycine, 0.1M, gives an immunoglobulin preparation that is substantially free of albumin and other serum proteins.

Immunoaffinity chromatography is performed to obtain a preparation with a higher fraction of specific antigen-binding antibody. The peptide used to raise the antiserum is immobilized on a chromatography resin and the specific antibodies directed against its epitopes are adsorbed to the resin. After washing away non-binding components, the specific antibodies are eluted with 0.1M glycine buffer, pH 2.3; antibody fractions are immediately neutralized with 1.0M Tris buffer, pH 8.0, to preserve immunoreactivity. The resin chosen depends on the reactive groups present in the peptide. If the peptide has an amino group, a resin such as Affi-Gel 10 or Affi-Gel 15 is used (Bio-Rad, Hercules, Calif.). If coupling through a carboxy group on the peptide is desired, Affi-Gel 102 can be used (Bio-Rad, Hercules, Calif.). If the peptide has a free sulfhydryl group, an organomercurial resin such as Affi-Gel 501 can be used (Bio-Rad, Hercules, Calif.).

Alternatively, spleens can be harvested and used in the production of hybridomas to produce monoclonal antibodies.

Example 15

Western Blotting of tissue samples

Tissue samples are homogenized in SDS-PAGE sample buffer (50 mM Tris-HCl, pH 6.8, 100 mM dithiothreitol, 2% SDS, 0.1% bromophenol blue, 10% glycerol), heated at 100° C. for 10 min and run on a 14% SDS-PAGE with a mM Tris-HCl, pH 8.3, 250 mM Glycine, 0.1% SDS running buffer. The proteins are electrophoretically transferred to nitrocellulose in a transfer buffer containing 39 mM glycine, 48 mM Tris-HCl, pH 8.3, 0.037% SDS, 20% methanol. The nitrocellulose is dried at room temperature for 60 min and then blocked with a PBS solution containing either bovine serum albumin or 5% nonfat dried milk for 2 h at 4° C.

The filter is placed in a heat-sealable plastic bag containing a solution of 5% nonfat dried milk in PBS with a 1:100 to 1:2000 dilution of affinity purified anti-EST peptide antibodies (see example 14), incubated at 4° C. for 2 h, followed by 3 10 min washes in PBS. An alkaline phosphatase conjugated secondary antibody, anti-mouse/rabbit IgG, is added at a 1:200 to 1:2000 dilution to the filter in a 150 mM NaCl, 50 mM Tris-HCl, pH 7.5 buffer and incubated for 1 h at room temperature.

The bands are visualized upon the addition and development of a chromogene substrate such as 5-bromo-4-chloro-3-indolyl phosphate/nitro blue tetrazolium (BCIP/NBT). This chromogene solution contains 0.033% NBT and 0.016% BCIP in a solution containing 100 mM NaCl, 5 mM MgCl$_2$ and 100 mM Tris-HCl, pH 9.5. The filter is incubated in the solution at room temperature until the bands develop to the desired intensity. Development is stopped in a PBS buffer containing 2 mM EDTA. Molecular mass determination is made based upon the mobility of pre-stained molecular weight standards (Rainbow markers, Amersham, Arlington Heights, Ill.).

Example 16

EIA Microtiter Plate Assay

To demonstrate how relative immunoreactivity for EST synthetic peptides is measured, wells of 96-well microtiter plates (Dynatec Immunolon 4 polystyrene) are coated for 16 h at 4° C. with 100 μl of the EST peptide at the following concentrations: 500 μM, 50 μM, 5 μM, 0.5 μM, 0.05 μM, and 0.005 μM. The buffer used for the application of these peptides is 100 mM morpholino-ethane sulfonic acid, pH 5.5. The EST peptides coated wells are then washed 3 times with wash buffer (8 mM sodium phosphate, 2 mM potassium phosphate, 140 mM sodium chloride, 10 mM potassium chloride, 0.05% Tween 20, 0.1% bovine serum albumin, pH 7.4).

The wells then are blocked for 1 h at room temperature with 9% w/v of Carnation skim milk powder in phosphate buffered saline (8 mM sodium phosphate, 2 mM potassium phosphate, 140 mM sodium chloride, 10 mM potassium chloride, pH 7.4). The wells next are washed 3 times with wash buffer.

The test specimen or control (mouse or rabbit antiserum) is diluted 150-fold with 4.5% Carnation skim milk powder in PBS. Then, 100 μl of this sample are incubated in the wells at 37° C. for 1 h, followed by 3 washes with wash buffer.

Horseradish peroxidase conjugated goat anti-mouse/rabbit IgG is used as a second antibody label to bind with the anti-EST-antibody/EST antigen complex formed in positive wells. 100 μl of HRPO-goat anti-mouse/rabbit IgG conjugate at a dilution of about 1:5000 in wash buffer are added to each well and incubated at room temperature for 1 h. The wells are washed 3 times with wash buffer.

Positive wells are identified by the absorbance readings at 405 nm after exposure of the wells to 100 μl of ABTS solution (2,2'-azinobis-[3-ethylbenzothizoline-6-sulfonic acid] diammonium salt) (Pierce Chemical Co., LOCATION). Alternatively, color development can be achieved with the addition to each well of 100 μl of a solution of o-phenylene diamine (OPD) in hydrogen peroxide, and a 10 min incubation at room temperature. The color development reaction is quenched with 100 μl of 1N sulfuric acid. The colors in the wells are read as absorbance with a Dynatech MR5000 plate reader at 490 nm and 630 nm wavelengths. A positive signal is indicative the presence of anti-EST peptide antibodies.

Example 17

Coating of Solid Phase Particles

A. Coating of Microparticles with Anti-EST Peptide Antibody

Affinity purified anti-EST peptide antibodies (see example 14) are coated onto microparticles which may include polystyrene, carboxylated polystyrene, polymethylacrylate or similar particles with a radius in the range of about 0.1 to 20 μm. Microparticles may be either passively or actively coated. One method is coating of EDAC (1-(3-dimethylaminopropyl)-3-ethylcarbodiimide hydrochloride (Aldrich Chemical. Co., Milwaukee, Wis.) activated carboxylated latex microparticles with anti-EST antibody. Briefly, a final 0.375% solid solution of resin washed carboxylated latex microparticles are mixed in a solution containing 50 mM MES buffer, pH 4.0 and 150 mg/l of affinity purified anti-EST antibody (see example 14) for 15 min in an appropriate container. EDAC coupling agent is added to a final concentration of 5.5 μg/ml to the mixture and mixed for 2.5 h at room temperature.

The microparticles then are washed with 8 volumes of a Tween 20®/sodium phosphate, pH 7.2 wash buffer by tangential flow filtration using a 0.2 μm Microgon Filtration module. Washed microparticles are stored in an appropriate buffer, usually containing a dilute surfactant and irrelevant protein as a blocking agent, until needed.

B. Coating of ¼ inch Beads

Anti-EST antibodies also may be coated on the surface of ¼ inch polystyrene beads by routine methods known in the art (Snitman et al, U.S. Pat. No. 5,273,882, incorporated herein by reference) and used in competitive binding or EIA sandwich assays. Polystyrene beads are first cleaned by ultrasonicating them for about 15 seconds in 10 mM NaHCO3 buffer at pH 8.0. The beads are then washed in deionized water until all fines are removed. Beads are then immersed in an antibody solution in 10 mM carbonate buffer, pH 8 to 9.5. The antibody solution can be as dilute as 1 μg/ml in the case of high affinity monoclonal antibodies or as concentrated as about 500 μg/ml for polyclonal antibodies which have not been affinity purified. Beads are coated for at least 12 hours at room temperature and then washed with deionized water. Beads may be dried or stored wet. They may be overcoated with protein stabilizers (sucrose) or non-specific binding blockers (irrelevant proteins, Carnation skim milk, or the like).

Example 18

Microparticle Enzyme Immunoassay (MEIA)

EST proteins and peptides are detected using a standard commercialized antigen competition EIA assay or polyclonal antibody sandwich EIA assay on the IMx® Analyzer (Abbott Laboratories, Abbott Park, Ill.). Briefly, samples suspected of containing the EST protein are incubated in the presence of anti-EST coated microparticles (see example 17). The microparticles are washed and secondary polyclonal anti-EST antibodies conjugated with detectable entities (i.e., alkaline phosphatase) are added and incubated with the microparticles. The microparticles are washed and the bound antibody/antigen/antibody complexes are detected by adding a substrate (i.e. 4-methyl umbelliferyl phosphate) (MUPP) that will react with the secondary conjugated antibody to generate a detectable signal. An elevated signal, indicating the presence of EST protein, is diagnostic of cancer.

Competitive binding assay uses a detectably labeled peptide that generates a specific background signal on the IMx® analyzer when the peptide is bound to an anti-peptide antibody coated microparticle. The labeled peptide also is added to the microparticles in the presence of patient samples suspected of containing the EST protein. The EST protein in the patient sample will compete with the labeled EST peptide for binding sites on the microparticle resulting in lowered IMx® signals. A lowered signal, indicating the presence of EST protein in the patient sample, is indicative of prostate tumor.

We claim:

1. A purified polynucleotide derived from a gene of a rapidly proliferating tissue which selectively hybridizes to the genome of prostate tumor or the complement thereof wherein said polynucleotide is selected from the group consisting of SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8, SEQUENCE ID NO 9 and complements thereof.

2. The polynucleotide of claim 1 wherein said polynucleotide is produced by recombinant techniques.

3. The recombinant polynucleotide of claim 2 wherein said recombinant polynucleotide comprises a sequence that encodes at least one epitope of prostate tumor.

4. A recombinant expression system comprising an open reading frame of DNA or RNA derived from a prostate tumor gene wherein said open reading frame comprises a sequence of prostate tumor genome or cDNA selected from the group consisting of SEQUENCE ID NOS 1 to 9 and complements thereof, and wherein said open reading frame is operably linked to a control sequence compatible with a desired host.

5. A host cell transformed with the recombinant expression system of claim 4.

6. A diagnostic reagent comprising a polynucleotide derived from prostate tumor gene wherein said polynucleotide or fragment thereof encodes at least one epitope of prostate tumor gene, wherein said epitope has at least 35% identity to polynucleotide selected from the group consisting of SEQUENCE ID NOS 1 to 9.

7. An oligonacleotide probe or primer comprising approximately at least about 6 nucleotides of a sequence selected from the group consisting of SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8 and SEQUENCE ID NO 9.

8. An oligonucleotide probe or primer comprising at least about 8 nucleotides of a sequence selected from the group consisting of SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8 and SEQUENCE ID NO 9.

9. An oligonucleotide probe or primer comprising at least about 10–12 nucleotiles of a sequence selected from the group consisting of SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8 and SEQUENCE ID NO 9.

10. An oligonucleotide probe or primer comprising at least about 15–20 nucleotides of a sequence selected from the group consisting of SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8 and SEQUENCE ID NO 9.

* * * * *